(12) United States Patent
Laufenberg et al.

(10) Patent No.: US 11,990,263 B2
(45) Date of Patent: May 21, 2024

(54) SMALL APPLIANCE

(71) Applicant: ETO MAGNETIC GmbH, Stockach (DE)

(72) Inventors: Markus Laufenberg, Stockach (DE); Thomas Schiepp, Seitingen-Oberflacht (DE); René Schnetzler, Messkirch (DE); Harald Eckhardt, Uhldingen-Muehlhofen (DE); Anton Blank, Stuttgart (DE)

(73) Assignee: ETO MAGNETIC GmbH, Stockach (DE)

( * ) Notice: Subject to any disclaimer, the term of this patent is extended or adjusted under 35 U.S.C. 154(b) by 1209 days.

(21) Appl. No.: 16/617,829

(22) PCT Filed: May 29, 2018

(86) PCT No.: PCT/EP2018/064011
§ 371 (c)(1),
(2) Date: Nov. 27, 2019

(87) PCT Pub. No.: WO2018/219912
PCT Pub. Date: Dec. 6, 2018

(65) Prior Publication Data
US 2021/0005372 A1 Jan. 7, 2021

(30) Foreign Application Priority Data

May 29, 2017 (DE) ..................... 10 2017 111 642.7

(51) Int. Cl.
H01F 10/14 (2006.01)
A61C 17/16 (2006.01)
(Continued)

(52) U.S. Cl.
CPC ............. *H01F 10/14* (2013.01); *A61C 17/16* (2013.01); *A61M 37/0076* (2013.01);
(Continued)

(58) Field of Classification Search
CPC .......... H01F 10/14; H01F 1/047; H01F 1/083; A61C 17/16; A61C 2201/007;
(Continued)

(56) References Cited

U.S. PATENT DOCUMENTS 3,375,820 A 4/1968 Kuris et al.
4,333,197 A * 6/1982 Kuris ................. A61C 17/3481
433/119
(Continued)

FOREIGN PATENT DOCUMENTS

CH 609 238 A5 2/1979
DE 601 15 989 T2 9/2006
(Continued)

OTHER PUBLICATIONS

Office Action dated Nov. 4, 2020 issued in corresponding JP patent application No. 2019-566279 (and English Summary of Office Action).

(Continued)

Primary Examiner — Shawki S Ismail
Assistant Examiner — Lisa N Homza
(74) Attorney, Agent, or Firm — POSZ LAW GROUP, PLC

(57) ABSTRACT

A small appliance device, in particular a body-care appliance device, in particular a shaving apparatus device, beard-trimming device, hair-trimming device, epilating appliance device, tattooing appliance device, toothbrush device or the like, has a drive unit which comprises at least one drive element, wherein the drive element comprises at least one magnetically shape-shiftable material.

24 Claims, 9 Drawing Sheets

Figure 1:
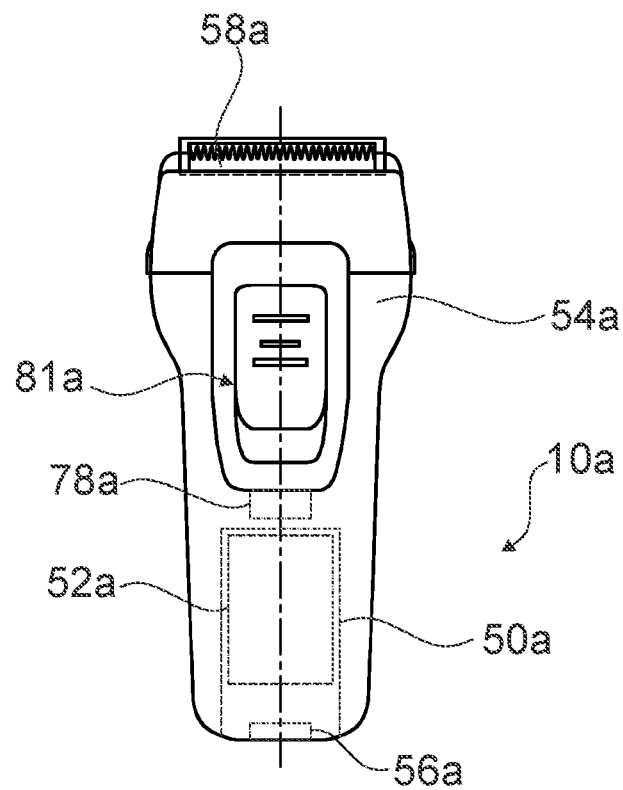

(51) Int. Cl.
*A61M 37/00* (2006.01)
*B26B 19/28* (2006.01)
*H02N 2/06* (2006.01)

(52) U.S. Cl.
CPC ............ *B26B 19/282* (2013.01); *H02N 2/06*
(2013.01); *A61C 2201/007* (2013.01)

(58) Field of Classification Search
CPC ... A61M 37/0076; B26B 19/282; H02N 2/06;
H02N 2/002; H10N 35/00
USPC ........................................................ 335/296
See application file for complete search history.

(56) References Cited

U.S. PATENT DOCUMENTS

| | | | | |
|---|---|---|---|---|
| 5,901,030 | A * | 5/1999 | Logan | H02N 13/00 |
| | | | | 279/128 |
| 6,157,101 | A * | 12/2000 | Ullakko | H10N 35/00 |
| | | | | 310/26 |
| 6,384,952 | B1 * | 5/2002 | Clark | G02B 26/06 |
| | | | | 359/223.1 |
| 6,515,382 | B1 | 2/2003 | Ullakko | |
| 6,552,839 | B1 * | 4/2003 | Hong | H02N 1/006 |
| | | | | 359/290 |
| 7,071,109 | B2 * | 7/2006 | Novotny | G02B 26/0841 |
| | | | | 438/719 |
| 7,200,298 | B2 * | 4/2007 | Kimura | G02B 26/0808 |
| | | | | 385/47 |
| 7,276,997 | B2 * | 10/2007 | Lvovsky | A61B 5/055 |
| | | | | 335/299 |
| 7,280,016 | B2 * | 10/2007 | Taya | B64C 21/02 |
| | | | | 335/78 |
| 7,286,033 | B2 * | 10/2007 | Ozaki | H01F 6/00 |
| | | | | 335/299 |
| 7,535,329 | B2 * | 5/2009 | Gorshkov | G01R 33/3806 |
| | | | | 335/302 |
| 7,719,396 | B2 * | 5/2010 | Umeda | H02K 33/16 |
| | | | | 359/199.1 |
| 7,719,752 | B2 * | 5/2010 | Sampsell | G02B 5/284 |
| | | | | 359/290 |
| 8,022,797 | B2 * | 9/2011 | Takeda | H02K 55/02 |
| | | | | 335/216 |
| 8,082,651 | B2 * | 12/2011 | Zaitsu | B81C 1/00174 |
| | | | | 29/469 |
| 8,237,525 | B2 * | 8/2012 | Hoang | F02M 51/0603 |
| | | | | 335/215 |
| 8,823,476 | B2 * | 9/2014 | Harrison | H01F 6/006 |
| | | | | 335/216 |
| 9,928,950 | B2 * | 3/2018 | Lubinski | H01F 41/02 |
| 10,069,392 | B2 * | 9/2018 | Degner | H02K 7/08 |
| 10,424,717 | B2 | 9/2019 | Schiepp et al. | |
| 11,264,158 | B2 * | 3/2022 | Sturcken | H01F 7/17 |
| 2003/0094861 | A1 | 5/2003 | Shimizu et al. | |
| 2003/0108439 | A1 | 6/2003 | Joshi | |
| 2006/0126151 | A1 * | 6/2006 | Aksyuk | G02B 26/0841 |
| | | | | 359/291 |
| 2006/0144472 | A1 | 7/2006 | Ullakko et al. | |
| 2006/0232368 | A1 * | 10/2006 | Gorshkov | G01R 33/3806 |
| | | | | 335/306 |
| 2007/0205853 | A1 * | 9/2007 | Taya | H10N 35/00 |
| | | | | 335/205 |
| 2007/0236314 | A1 * | 10/2007 | Taya | H02N 2/021 |
| | | | | 335/220 |
| 2007/0297042 | A1 * | 12/2007 | Bifano | G02B 26/02 |
| | | | | 359/318 |
| 2008/0012671 | A1 * | 1/2008 | Fortsch | H01H 27/007 |
| | | | | 335/229 |
| 2008/0055028 | A1 * | 3/2008 | Mask | A61M 37/0084 |
| | | | | 335/229 |
| 2008/0278789 | A1 * | 11/2008 | Tanaka | G02B 26/0825 |
| | | | | 359/224.1 |
| 2008/0316563 | A1 * | 12/2008 | Aksyuk | B81C 1/00476 |
| | | | | 359/224.1 |
| 2009/0031548 | A1 * | 2/2009 | Zaitsu | B81C 1/00174 |
| | | | | 29/445 |
| 2009/0115284 | A1 * | 5/2009 | Liang | H02N 2/021 |
| | | | | 310/300 |
| 2010/0085622 | A1 * | 4/2010 | Hofmann | B81C 1/00166 |
| | | | | 156/292 |
| 2010/0242673 | A1 * | 9/2010 | Laufenberg | F02D 9/1065 |
| | | | | 74/99 R |
| 2011/0013300 | A1 * | 1/2011 | Wu | G02B 26/0858 |
| | | | | 359/849 |
| 2011/0128521 | A1 * | 6/2011 | Weber | H02N 2/023 |
| | | | | 74/110 |
| 2012/0031360 | A1 * | 2/2012 | Laufenberg | F01L 1/46 |
| | | | | 123/90.17 |
| 2013/0038414 | A1 * | 2/2013 | Laufenberg | H10N 35/80 |
| | | | | 335/229 |
| 2013/0088313 | A1 * | 4/2013 | Harrison | H01F 6/00 |
| | | | | 335/216 |
| 2013/0100519 | A1 * | 4/2013 | Daniel | H05B 33/12 |
| | | | | 359/290 |
| 2014/0002218 | A1 * | 1/2014 | Bory | H01F 7/122 |
| | | | | 335/229 |
| 2014/0085740 | A1 * | 3/2014 | Rooms | G02B 26/06 |
| | | | | 359/846 |
| 2014/0091646 | A1 * | 4/2014 | Schiepp | H02N 2/00 |
| | | | | 310/26 |
| 2015/0054359 | A1 * | 2/2015 | Schiepp | H10N 35/00 |
| | | | | 310/26 |
| 2015/0131135 | A1 * | 5/2015 | Reinmuth | G02B 26/0841 |
| | | | | 438/26 |
| 2015/0192218 | A1 * | 7/2015 | Arend | F16K 31/0679 |
| | | | | 310/38 |
| 2016/0087553 | A1 * | 3/2016 | Müllner | F04B 17/03 |
| | | | | 335/215 |
| 2016/0148736 | A1 * | 5/2016 | Schiepp | H01F 7/18 |
| | | | | 335/268 |
| 2016/0204716 | A1 * | 7/2016 | Suzuki | H02N 1/008 |
| | | | | 251/129.01 |
| 2016/0233408 | A1 * | 8/2016 | Schiepp | H10N 35/00 |
| 2016/0377858 | A1 * | 12/2016 | Hester | G02B 26/0841 |
| | | | | 359/221.2 |
| 2019/0039881 | A1 * | 2/2019 | Starman | B81B 3/0043 |
| 2019/0049034 | A1 * | 2/2019 | Ohrem | F16K 31/007 |
| 2019/0089268 | A1 * | 3/2019 | Patel | F03G 7/065 |
| 2019/0109546 | A1 | 4/2019 | Blank | |
| 2019/0121120 | A1 * | 4/2019 | Schiepp | F16K 31/025 |
| 2019/0187943 | A1 * | 6/2019 | Sasaki | G06F 3/1278 |
| 2019/0304651 | A1 * | 10/2019 | Laufenberg | H01F 7/1646 |
| 2020/0111633 | A1 * | 4/2020 | Schautzgy | H01H 71/145 |
| 2020/0152364 | A1 * | 5/2020 | Sturcken | H01F 7/17 |
| 2020/0211418 | A1 * | 7/2020 | Greiner | G09B 21/003 |
| 2020/0303622 | A1 * | 9/2020 | Schnetzler | H10N 35/00 |
| 2021/0246891 | A1 * | 8/2021 | Schautzgy | H10N 35/85 |

FOREIGN PATENT DOCUMENTS

| | | |
|---|---|---|
| DE | 10 2011 052 528 B3 | 2/2013 |
| DE | 10 2013 110 131 A1 | 3/2015 |
| DE | 102013110131 A1 | 3/2015 |
| EP | 0 885 698 A1 | 12/1998 |
| JP | 2004-298246 A | 10/2004 |
| JP | 2006-521198 A | 9/2006 |
| JP | 2016-533644 A | 10/2016 |
| WO | 92/13395 A1 | 8/1992 |
| WO | 2006/013395 A1 | 2/2006 |
| WO | 2017/167684 A1 | 10/2017 |

OTHER PUBLICATIONS

Search Report dated Mar. 16, 2018 issued in corresponding DE patent application No. 10 2017 111 642.7 (and partial English translation).

(56) References Cited

OTHER PUBLICATIONS

International Search Report dated Oct. 1, 2018 issued in corresponding International Patent Application No. PCT/EP2018/064011.
International Preliminary Report on Patentability dated Dec. 3, 2019 issued in corresponding International Patent Application No. PCT/EP2018/064011.
Chinese Office Action dated Mar. 16, 2023 issued in corresponding CN Application No. 201880048223.1 (and partial English translation).
European Office Action dated Nov. 5, 2021 issued in corresponding EP Application No. 18729897.1 ( and English Translation).
Japanese Office Action dated Apr. 6, 2021, issued in corresponding JP Patent Application No. 2019-566279 (and English Machine Translation).

* cited by examiner

SMALL APPLIANCE

CROSS REFERENCE TO RELATED APPLICATIONS

This application is a U.S. national stage application of PCT/EP2018/064011 filed on May 29, 2018, which is based on German Patent Application No. 10 2017 111 642.7 filed on May 29, 2017, the contents of which are incorporated herein by reference.

PRIOR ART

The invention relates to a small appliance device according to the preamble of claim 1.

Small appliances, in particular for body treatment and/or body care, for example shavers, tattooing appliances, beard trimmers, electric toothbrushes and the like, which comprise an electric motor as a drive, are already known. In this case, eccentrics are often used in order to convert a rotational movement into a linear movement.

The object of the invention is, in particular, to provide an apparatus of the species having improved properties in respect of handling. It is furthermore an object of the invention, in particular, to achieve high convenience of use. It is furthermore an object of the invention, in particular, to achieve advantageous properties in respect of variability.

Advantages of the Invention

The invention relates to a small appliance device, preferably an electrical small appliance device, preferably a small electric appliance device, in particular a body-care appliance device and/or a body-treatment appliance device, for example a shaving apparatus device, a beard-trimming device, a hair-trimming device, an epilating appliance device, a tattooing appliance device, a pricking appliance device, a piercing device, a toothbrush device, or the like, having at least one drive unit which comprises at least one drive element.

It is proposed that the drive element comprise at least one magnetically shape-shiftable material.

By the implementation according to the invention of the small appliance device, advantageous handling may be achieved. Furthermore, high convenience of use and/or high operating convenience may be achieved. In addition, a high variability and/or flexibility may be achieved, particularly in respect of adaptation to a field of application. Furthermore, a small appliance device having an advantageous, in particular precisely operating and/or precisely adjustable and/or simply and/or precisely drivable drive may be provided. Furthermore, a drive having a wide range in respect of possible movement speeds and/or movement frequencies and/or in respect of a movement scope may be achieved. In addition, a high acceleration of moving component parts and/or advantageous force exertion may be achieved so that, in particular in a corresponding application, for example hair may be shortened and/or removed efficiently and/or reliably and/or precisely and/or painlessly. In particular, short field pulses which are simple to generate may be used for reliable generation of spontaneously occurring and/or very rapid movements. In addition, very low noise production of a drive may advantageously be achieved. Furthermore, an advantageous movement may be generated economically and/or simply and/or reliably with short repetition rates and/or in single-pulse operation, in particular a pulse-like movement. Furthermore, a small appliance having a drive operating in a pulse-like fashion may be provided, which in particular allows adaptation to different fields of use and/or fields of application. In particular for cutting and/or piercing and/or extracting processes, an abruptly and/or spontaneously occurring, advantageously more square-wave than sinusoidal, movement may advantageously be generated.

A "small appliance device" is, in particular, to mean an, in particular functionally capable, component, in particular a structural and/or functional component, of a small appliance, in particular of an electrical small appliance, which is preferably configured for use in a state held, in particular with a hand, by a user. In particular, the small appliance device is implemented as a small electric appliance device and/or a small household appliance device, in particular as an electric small household appliance device. In particular, the small appliance device may comprise the entire small appliance and/or be implemented as the small appliance. Advantageously, the small appliance is implemented as a small electric appliance and/or as a small household appliance, in particular as an electric small household appliance. In particular, the small appliance is portable and/or can be transported by a single person. In particular, the small appliance has a total mass of at most 20 kg, advantageously of at most 10 kg, particularly advantageously at most 5 kg and preferably at most 2 kg, and in particular at most 1 kg or at most 500 g. Advantageously, the small appliance device is configured for connection to a network voltage, preferably an AC network voltage, in particular to a network voltage other than a high voltage, advantageously to a network voltage of a low-voltage network, for example of 100 V or 110 V or 120 V or 220 V or 230 V or 240 V or any other, in particular conventional, voltage value as a supply voltage, in which case both connection to a charge, for example an internal energy store, preferably if the small appliance device is implemented for example as a portable battery-operated small appliance device, and, in particular as an alternative or in addition, connection to a direct energy supply of the small appliance device, preferably if the small appliance device is embodied as a cabled small appliance device, may be envisioned. The term "configured" is in particular to mean specifically programmed, designed and/or implemented. That an object is configured for a particular function is, in particular, to mean that the object fulfills and/or carries out this particular function in at least one application state and/or operating state.

In particular, the drive unit is configured to generate at least one, in particular repetitive and/or pulsed and/or pulse-like, drive movement. Advantageously, at least one drive parameter of the drive unit is pre-determinable and/or selectable and/or drivable. The drive parameter may, for example, be a repetition rate and/or an amplitude and/or an actuation force and/or a movement direction and/or a characteristic curve, in particular an actuation position/actuation force characteristic curve. Advantageously, the drive unit is connectable and/or connected to at least one driven unit of the small appliance device and/or of the small appliance. The driven unit may in particular comprise at least one working tool, for example a shaving head and/or a cutting blade and/or an epilation element, in particular an epilation roller, and/or a needle and/or a brush head or the like.

Preferably, the drive element is configured to generate at least one actuation movement at least partially, in particular by at least partial deformation of the drive element. In this case, it is conceivable for the actuation movement to correspond to the drive movement. Preferably, the actuation movement and the drive unit extend parallel to one another and/or along a common axis. It is also conceivable for the drive unit to comprise at least one transmission unit, which is configured to convert the actuation movement into the drive movement, the transmission unit comprising in particular at least one transmission element, for example a gearwheel, a friction wheel, a lever, a pusher, a gearing, a cam disk or the like. In particular, an actuation movement generated directly by the drive element is different to a rotation movement. Advantageously, the drive unit is free of an eccentric and/or of component parts for converting a rotational movement into a linear movement. In particular, the actuation movement is a linear movement, in particular along an axis, in particular along the longitudinal axis of the drive element. Preferably, the drive element is a magnetically shape-shiftable drive element. In particular, the drive element is formed in one piece and/or as a solid body. It is, however, also conceivable for the activating element, in particular at least in sections, to be implemented as a hollow body, for example as a hollow cylinder, and/or as a solid body having recesses and/or cavities of the like. Preferably, the activating element is formed at least predominantly, in particular fully, from the shape-shiftable material. In principle, it is of course conceivable for the drive unit to comprise a multiplicity of drive elements, in particular formed identically to one another or differently. In particular, a plurality of actuation elements may be arranged next to one another or behind one another and/or connected in series and/or parallel in terms of action, or adaptation of a total excursion and/or a total actuation force. Preferably, the drive element, in particular at least in sections, is implemented elongately and/or in the shape of a pin and/or in the shape of a plunger and/or as a cuboid and/or cylindrically. Particularly preferably, the drive element has an at least substantially constant cross section, in particular along its longitudinal axis. Preferably, the longitudinal axis of the drive element is arranged at least substantially parallel to a main extent direction of the drive element or at least substantially perpendicularly thereto. Particularly preferably, the longitudinal axis of the drive element is arranged at least substantially parallel or at least substantially perpendicularly to a movement direction of the actuation movement.

A "main extent direction" of an object is, in particular, to mean a direction which extends parallel to a longest edge of a smallest imaginary cuboid that just fully encloses the object. Here, "at least substantially parallel" is to mean an orientation of a direction relative to a reference direction, particularly in a plane, the direction having a deviation from the reference direction in particular by less than 8°, advantageously less than 5° and particularly advantageously less than 2°. Here, "at least substantially perpendicular" is to mean an orientation of a direction relative to a reference direction, particularly in a reference plane, the direction and the reference plane making an angle which deviates from a right angle in particular by less than 8°, advantageously less than 5° and particularly advantageously less than 2°. That an object has an "at least substantially constant cross section" is in particular to mean, in this context that, for an arbitrary first cross section of the object along at least one direction and an arbitrary second cross section of the object, a minimum surface area of a differential surface which is formed when superimposing the cross sections is at most 20%, advantageously at most 10% and particularly advantageously at most 5% of the surface area of the larger of the two cross sections.

Preferably, the drive element is configured to convert at least one external stimulus, in particular at least one magnetic signal, into the actuation movement. In particular, the drive element is configured to shape-shift as a function of the external stimulus, in particular by means of at least one contraction and/or by means of at least one expansion, preferably in a direction at least substantially parallel to the longitudinal axis of the drive element, preferably while keeping a volume of the drive element constant. In particular, generation of an actuation movement involves a length change of the drive element, in particular along its longitudinal axis, by at least 1.5%, advantageously by at least 2%, particularly advantageously by at least 3% and preferably by at least 4%, even greater length changes, for example by at least 5% or by at least 6% being conceivable. Furthermore, an in particular magnetically induced shape shift of the drive element, particularly in order to generate the actuation movement, involves a force exertion advantageously acting substantially parallel to the longitudinal axis of the drive element, in particular in an actuation direction, of at least 1 N, preferably at least 1.5 N, more preferably at least 2 N per $mm^2$ of cross-sectional area of the drive element, in particular of a cross section perpendicular to the longitudinal axis of the drive element. The magnetically shape-shiftable material may, for example, be a magnetostrictive material. Advantageously, however, the magnetically shape-shiftable material is a magnetically effective and/or active shape-memory material, in particular a magnetic shape-memory material, and particularly preferably a magnetic shape-memory alloy (also known as MSM material=Magnetic Shape Memory). In this way, in particular, particularly simple deformation may be produced with an advantageously large movement range.

In an advantageous implementation of the invention, it is proposed that the magnetically shape-shiftable phase in material be monocrystalline. Preferably, the drive element is formed as a single crystal from the magnetically shape-shiftable material. It is also conceivable for the activating element to be composed of a plurality of, in particular from a few, for example from two or three or four or five individual single crystals. In this way, in particular, an advantageously large stroke effect may be produced. It is, however, also conceivable for the magnetically shape-shiftable material to be implemented in the polycrystalline fashion.

Preferably, the shape-shiftable material contains nickel, manganese and gallium. Particularly preferably, the shape-shiftable material is a nickel-manganese-gallium alloy. In particular, the magnetically shape-shiftable material contains at least 20%, advantageously at least 30%, particularly advantageously at least 40% and preferably at least 45% and/or at most 80%, advantageously at most 70%, particularly advantageously at most 60% and preferably at most 55% nickel, preferably expressed in terms of weight. Furthermore, the magnetically shape-shiftable material contains in particular at least 10%, advantageously at least 15% and particularly advantageously at least 20% and/or at most 50%, advantageously at most 40%, particularly advantageously at most 35% and preferably at most 30% manganese, preferably expressed in terms of weight. In addition, the magnetically shape-shiftable material contains in particular at least 10%, advantageously at least 15% and particularly advantageously at least 20% and/or at most 50%, advantageously at most 40%, particularly advantageously at most 35% and preferably at most 30% gallium, preferably expressed in terms of weight. In this way, in particular, a particularly easily achievable deformability with an advantageously large movement range may be produced.

As an alternative, the shape-shiftable material may also be an iron-palladium alloy and/or an iron-palladium-containing alloy. In addition, the shape-shiftable material could also be embodied as a foam and/or as a composite structure and/or as granules and/or as a porous material, particularly in the case of a composite material it being conceivable that nickel, manganese and/or gallium constituents, advantageously pieces and/or crystallites of NiMnGa, may be embedded in a matrix.

High reliability and/or economical producibility may, in particular, be achieved if the drive element is embodied as a solid body.

In another implementation of the invention, it is proposed that the drive unit comprise at least one magnet unit, which is configured to generate at least one time-variable shape-shiftable magnetic field for the drive element. Preferably, the magnet unit is drivable. In particular, the magnet unit is configured to generate at least one, in particular correspondingly, time-variable magnetic field as a function of at least one drive signal, in particular of a time-variable actuation current and/or of a time-variable actuation voltage. Advantageously, the magnet unit comprises at least one magnet element, in particular an inductive magnet element, preferably a coil. Particularly advantageously, the small apparatus comprises at least one control and/or regulating unit which is configured to drive the magnet unit, in particular as a function of an operating mode, which is for example selectable by a user. It is conceivable for the control and/or regulating unit to comprise at least one, in particular wireless, interface for connection to an in particular external database, via which parameters may be retrieved from the external database as a function of the operating mode and/or as defined by the operating mode. For example, application-specific drive parameters, for example a characteristic of magnetization pulses, an actuation force, an actuation movement, PID values for regulation of a magnetization and/or of a movement of the drive element and the like may be stored and/or storable in the control and/or regulating unit and/or callable from the database and/or may define operating states, for example for treatment and/or care of skin parts with different natures, of users and/or patients of different sexes, different skin color, different age and the like, or any other operating states. In particular, the magnet unit is configured in at least one operating state, particularly in a pulsed operating state, to generate individual, preferably square-wave and/or sawtooth and/or triangular and/or bell-shaped magnetic field pulses, advantageously at, in particular regular, time intervals which are selectable and/or dependent on an operating mode. In this way, a high variability may be achieved in respect of generatable movements. Furthermore, in this way a type and/or a scope and/or a repetition rate of a movement may be adapted precisely and/or reliably.

It is also conceivable for the drive unit to be operable in a single-pulse mode, in which in particular a single cutting movement may be initiated by the user, for example by pressing a button. In addition, arbitrary repetition rates for the drive movement may be envisioned, in particular even very slow repetition rates such as for example less than 100 Hz, less than 50 Hz, less than 20 Hz or even less than 10 Hz. Furthermore, even repetition rates of less than 1 Hz may be envisioned. In principle, the drive element allows an arbitrary reduction of a movement frequency, even though a movement speed and/or a movement acceleration may assume a high value and, in particular, not need to be reduced with the frequency. In particular, reliable functioning of a small appliance, in particular reliable generation of a cutting, piercing, shaving and/or tearing movement, may be made possible in this way, advantageously without having to increase a number of corresponding movements per unit time. In particular, by means of the drive element, may It is furthermore proposed that the magnet unit comprise at least one coil element, which at least partially encompasses the drive element, in particular its longitudinal axis. Preferably, the coil element fully encompasses the drive element as seen along the longitudinal axis of the drive element. Particularly preferably, a coil axis of the coil element corresponds to the longitudinal axis of the drive element. In particular, the drive element is arranged inside the coil element. Advantageously, the coil element has a length, in particular along its coil axis, which corresponds to at least 50%, advantageously at least 60%, particularly advantageously at least 70%, preferably at least 80% and particularly preferably at least 90% of a length of the drive element, in particular along the longitudinal axis of the drive element. In particular, the coil element generates in at least one operating state, particularly in the event of actuation and/or for generation of an actuation movement, a magnetic field whose field lines extend at least substantially parallel to the longitudinal axis of the drive element at least in sections, particularly in a region arranged inside the coil element and inside the drive element which advantageously extends over at least 50%, particularly advantageously over at least 60%, and preferably over at least 70%, of the length of the coil element and/or the length of the drive element. Preferably, the drive unit is, particularly in this case, free of a magnetic circuit. Particularly preferably, the coil element is implemented as an air-core coil. In this way, a high installation space efficiency may advantageously be achieved, particularly in respect of arrangement of a coil and of a drive element. In addition, a short reaction time and/or a spontaneous response behavior may be achieved. As an alternative or in addition it is conceivable that the magnet unit comprises at least one coil element which is arranged next to the drive element. Furthermore, it is conceivable for the magnet unit to comprise at least one magnetic circuit which is configured to introduce the shape-shiftable magnetic field into the drive element. In general, it is conceivable for the magnet unit to be configured to generate the shape-shiftable magnetic field in such a way that its field lines extend at least substantially perpendicularly or, as an alternative, at least substantially parallel to the longitudinal axis of the drive element, particularly in a region of the drive element and/or inside the drive element. Preferably, a contraction or an expansion of the drive element may selectively be generated in this way.

A coil element may in this case comprise and/or be implemented as at least one wire coil and/or at least one ribbon coil, in particular having at least one conductor made of copper and/or aluminum and/or another highly conductive metal, and/or be implemented as such. Preferably, the coil element is implemented to be low-ohmic, so that because of a low inductance a magnetic field may advantageously be set up within a short time. The shape-shiftable magnetic field is, in particular, generated by means of energizing the coil element. Advantageously, particularly in pulsed operation, an individual energizing time of the coil element is at most 20 ms, particularly advantageously at most 10 ms, preferably at most 5 ms particularly preferably at most 2 ms.

In a preferred implementation of the invention, it is proposed that the magnet unit be configured to initiate a contraction of the drive element parallel to the actuation direction. In particular, the actuation device is arranged at least substantially parallel to the longitudinal axis of the drive element. Advantageously, in a non-actuated state, the drive element is in an expanded state and/or pre-stressed with a tension along its longitudinal axis. Advantageously, in this case the actuation movement is generated by means of contraction of the drive element. In this way, advantageous properties may be achieved in respect of movement generation.

In an advantageous implementation of the invention, it is proposed that the small appliance device comprise a reset unit, which is configured to apply a reset force to the drive element. It is conceivable for the reset unit to be part of the drive unit. It is also conceivable for the reset unit and the drive unit to be formed at least partially in one piece. It is furthermore conceivable for the reset unit and the drive unit to be formed separately from one another. Preferably, the reset force counteracts a force generated during the generation of the actuation movement. In particular, the reset force acts in a direction at least substantially parallel to the longitudinal axis of the drive element. It is also conceivable for the reset force to counteract an expansion or a contraction of the drive element in a direction perpendicular to the longitudinal axis of the drive element. Preferably, the reset unit is configured for reverse deformation of the drive element, particularly after its deformation in order to generate the actuation movement. In particular, the reverse deformation may generate a further actuation movement, in particular directed oppositely to the actuation movement. In this way, controlled movement generation may advantageously be achieved.

It is furthermore proposed that the reset unit be configured to counteract a contraction of the drive element parallel to the actuation direction. Advantageously, the reset unit applies at least one tensile force to the drive element, particularly substantially parallel to the longitudinal axis of the drive element. Particularly in this case, the actuation movement is generated by means of a contraction of the drive element and a further actuation movement by means of a subsequent, in particular reversely deforming, expansion of the drive element, preferably in each case at least substantially parallel to the longitudinal axis of the drive element. In this way, an abrupt movement and/or a very high acceleration may be achieved, in particular together with a compact construction.

It is of course also conceivable for the reset unit to be configured to counteract an expansion of the drive element parallel to the actuation direction. Particularly in this case, it is conceivable for the reset unit to apply a compressive force to the drive element, in particular at least substantially parallel to the longitudinal axis of the drive element.

It is furthermore proposed that the reset unit comprise at least one reset element having a degressive spring characteristic curve. In this way, particularly for a given deflection, a high energy content of a reset element and/or effective reset operation may be achieved.

It is of course also conceivable for the reset unit, in particular as an alternative or in addition, to comprise at least one reset element having a progressive spring characteristic curve and/or at least one reset element having a linear spring characteristic curve. Irrespective of a shape of the spring characteristic curve, for example a spring element, in particular a helical spring element, for example a compression spring and/or a tension spring and/or a leaf spring and/or a cup spring and/or a torsion spring and/or another spring element, in particular bent suitably to achieve a desired spring characteristic curve, or the like may be envisioned as reset element. Furthermore, air springs and/or magnetic springs and/or other suitable reset elements may be envisioned, as well as in particular arbitrary combinations of suitable spring elements. Preferably, the reset element is configured to generate a compressive force and/or a tensile force as the reset force. In principle, however, it is also conceivable for a reverse deformation of the drive element to be generated by means of at least one flexion and/or shear and/or torsion. In addition, it is conceivable for the reset unit comprises at least one force converter, which is configured to transmit a reset force and/or change its direction. For example, by means of a corresponding force converter a tension spring may be used to apply a compressive force to the drive element and/or a compression spring may be used to apply a tensile force to the drive element. Furthermore, a plurality of reset elements may of course be arranged in such a way that they together generate a reset force.

It is furthermore proposed that the reset unit comprise at least one magnet element, in particular a permanent magnet element and/or an electromagnet element. Advantageously, the reset unit has at least one magnetic spring that comprises the magnet element. In particular, it is conceivable for the reset unit to comprise a combination of at least one magnetic spring with at least one mechanical spring. In this way, a spring characteristic curve may be flexibly adapted according to the application and/or according to requirements.

In an advantageous implementation of the invention, it is proposed that the drive element can be brought into at least one first stable expansion state, in particular an expansion at least substantially parallel to the longitudinal axis of the drive element, and into at least one second stable expansion state, in particular an expansion at least substantially parallel to the longitudinal axis of the drive element. In particular, at least one of the expansion states is different to a minimum expansion state and to a maximum expansion state of the drive element. It is also conceivable for the first stable expansion state and/or the second stable expansion state to correspond to final positions of the drive element. Particularly in this case, it is conceivable for an expansion of the drive element to move during operation between the first stable expansion state and the second stable expansion state. Of course, more than two stable expansion states may also be envisioned. It is furthermore conceivable for the drive element, at least over a particular expansion range, to be stable in arbitrary expansion states. Advantageously, the first stable expansion state and/or the second stable expansion state, preferably all the expansion states, are stable without energy being supplied. Preferably, the expansion states are generated or generatable by using a hysteresis of the magnetically shape-shiftable material. In this way, a high energy efficiency may advantageously be achieved. Furthermore, a high variability may be achieved in respect of movement states and resting positions that can be produced.

In a particularly advantageous implementation of the invention, it is proposed that the small appliance device comprise at least one holding unit, which is configured to stabilize the first stable expansion state and the second stable expansion state, and which comprises at least one holding magnet element. The holding magnet element may, for example, comprise and/or be embodied as at least one permanent magnet and/or at least one electromagnet. Advantageously, the holding unit comprises at least one pre-stressing unit which is configured to generate at least one pre-stressing force, in particular a compressive and/or a tensile force, for the drive element, and which preferably acts at least substantially parallel to its longitudinal axis. The holding unit, in particular the pre-stressing element, may be embodied at least partially in a one-part implementation with the reset unit, in particular with the reset element. Preferably, the holding unit is configured to generate at least one permanent magnetic field, which is applied to the drive element and in particular is superimposed on the shape-shiftable magnetic field and in particular either weakens or strengthens the latter depending on the operating state. In this way, different expansion states of the drive element may advantageously be stabilized reliably and/or energy-efficiently.

It is furthermore proposed that the holding magnet element comprise at least one magnetically reversible permanent magnet, which for example may be formed at least partially from an aluminum-nickel-cobalt alloy. In particular, the magnetically reversible permanent magnet is an AlNiCo magnet. Preferably, the magnet unit is configured to reverse the magnetization of the magnetically reversible permanent magnet by means of the shape-shiftable magnetic field. For example, the stable expansion states may be stabilized by magnetizing and/or by demagnetizing the magnetically reversible permanent magnet. In this way, construction simplicity may advantageously be achieved.

It is furthermore conceivable for the small appliance device to comprise at least one second drive unit, which is arranged antagonistically with respect to the drive unit. In particular, the second drive unit comprises at least one second drive element. Preferably, the drive unit and the second drive unit are arranged in such a way that an expansion of the drive element effects a compression of the second drive element, and preferably vice versa. The drive units may in this case be connected by means of at least one force converter. In particular, it is conceivable for the drive element and the second drive element to act on opposite sides of a rocker lever. Advantageously, the drive unit and the second drive unit are arranged opposite one another and/or coaxially. In particular, a longitudinal axis of the second drive element corresponds to the longitudinal axis of the first drive element. In particular, the drive unit and the second drive unit together form a bistable actuator, for example a push-push actuator or a pull-pull actuator. In this way, a precisely drivable actuator may advantageously be provided. Furthermore, end positions may be approached rapidly and/or reliably.

It is furthermore proposed that the second drive element comprise at least one magnetically shape-shiftable material. In particular, the second drive element is implemented as a magnetically shape-shiftable drive element. In particular, it is conceivable for the drive element and the second drive element to be at least substantially implemented identically and/or in particular mirror-symmetrically with respect to one another. Furthermore, the drive unit and the second drive unit may be at least substantially implemented identically and/or in particular mirror-symmetrically with respect to one another. In particular, it is conceivable for the second drive unit to form the holding unit at least partially. It is furthermore conceivable for the drive unit and the second drive unit to stabilize one another, particularly in respect of expansion states of the drive element and of the second drive element. "At least substantially identical" objects are in particular to mean objects which are designed in such a way that they can respectively fulfill a common function and differ in their design, apart from manufacturing tolerances, at most by individual elements that are not essential for the common function, and advantageously objects which are implemented identically apart from manufacturing tolerances and/or in the scope of manufacturing-technology possibilities, wherein identical objects are also, in particular, to mean mutually symmetrical objects. In this way, a precisely drivable and/or variably usable actuator having a spontaneous response behavior may be provided. Furthermore, a bistability of end positions may advantageously be achieved.

It is furthermore proposed that the small appliance device comprise at least one reluctance unit, which is configured to generate an assisting drive force and/or an assisting drive movement. Preferably, the drive unit is implemented as a hybrid drive unit, in particular as an MSM-reluctance hybrid drive unit. Advantageously, the reluctance unit is a portion of the drive unit and/or is at least partially embodied in a one-part implementation therewith. Preferably, the reluctance unit comprises at least one reluctance drive element which is configured to generate the assisting drive force and/or the assisting drive movement under the effect of the shape-shiftable magnetic field of the magnet unit. In this way, an actuation force and/or an actuation movement may advantageously be adapted variably.

It is furthermore proposed that the drive unit comprise at least one support element for the drive element, which is at least partially implemented integrally with the reluctance unit. In particular, the support element forms the reluctance drive element at least partially. Advantageously, the support element is embodied as an armature element, which is connected to the drive element and which forms the reluctance drive element. Preferably, the support element and/or the reluctance drive element are formed at least partially from a ferromagnetic material. In this way, a compact construction may advantageously be achieved.

In an advantageous implementation of the invention, it is proposed that the drive unit comprise at least one further drive element, which is connected in series with the drive element in respect of a drive effect, and the longitudinal axis of which is different to a longitudinal axis of the drive element. Advantageously the further drive element is implemented as a magnetically shape-shiftable drive element. Particularly advantageously, the further drive element comprises at least one magnetically shape-shiftable material. Preferably, the drive element and the further drive element are at least substantially implemented identically to one another. In particular, the drive element and the further drive element are arranged next to one another, in particular flush. Preferably, the drive unit comprises at least one stroke transmission element which is configured for coupling, in particular for at least partial addition, of a stroke generated by the drive element and of a stroke generated by the further drive element. In particular, the stroke transmission element is connected to a front front face of the drive element and to a rear front face of the further drive element. Advantageously, the stroke transmission element is implemented in the shape of a step. Advantageously, the drive element and the further drive element are arranged in a common magnetization region. Advantageously, the magnet unit is configured to provide the shape-shiftable magnetic field as a common shape-shiftable magnetic field for the drive element and the further drive element. It is, however, also conceivable for drive elements to be assigned different magnet units, for example in order to be able to precisely adjust an overall stroke. Of course, the drive unit may comprise any desired number of drive elements coupled in such a way, which may in particular, be implemented at least substantially identically to one another or differently. In this way, a large stroke may advantageously be achieved together with a compact construction.

It is furthermore proposed that the small appliance device comprise at least one energy supply unit, which comprises at least one energy store, in particular at least one capacitor and/or at least one battery, in particular a lithium-ion battery.

The energy supply unit may comprise an interface for connection to the mains voltage, for example for charging the energy store and/or for operating the drive unit. In particular, the energy supply unit is configured for a cabled energy supply of the drive unit and/or at least of control electronics.

Advantageous properties in respect of handling and/or variable and/or adaptable usability may be achieved particularly with a small appliance having at least one small appliance device according to the invention. For example, the small appliance may be embodied as a shaver, a beard trimmer, a hair trimmer, an epilating appliance, a tattooing appliance, a pricking appliance, a piercing appliance, an electric toothbrush or the like. The small appliance may furthermore be a combined device which, for example, combines at least two of the devices as described, or their functionalities, for instance a combined hair and beard trimmer, a shaver with an additional beard trimmer, an epilating appliance with an additional shaver, a combined tattooing and pricking appliance, or the like.

It is furthermore proposed that the small appliance device according to the invention and/or the small appliance according to the invention be used for body care and/or for body treatment, for example for shaving, for trimming hair, for trimming a beard, for epilation, for tattooing, for piercing, for cleaning teeth or the like. In this way, in particular, high convenience of use and/or advantageous handling may be achieved.

The invention furthermore relates to a method with at least one small appliance device according to the invention and/or with at least one small appliance according to the invention, wherein at least one body-care activity, for example shaving and/or trimming hair and/or epilation and/or cleaning teeth or the like, and/or at least one body treatment, for example tattooing and/or piercing and/or a skin treatment, in particular involving, pricking or the like is carried out. In particular, a high variability in respect of adaptation to an application and/or high convenience and/or high precision of a form of care and/or a treatment may be achieved by a corresponding method.

The invention furthermore relates to a method with at least one small appliance device according to the invention and/or with at least one small appliance according to the invention, at least one movement being generated by means of at least one magnetically induced shape shift of the drive element.

The invention furthermore relates to a method for producing a small appliance device according to the invention.

The small appliance device according to the invention, the small appliance according to the invention and the method according to the invention, are not intended in this case to be restricted to the applications and embodiments described above. In particular, the small appliance device according to the invention, the small appliance according to the invention and the method according to the invention may, in order to fulfill a functionality described here, comprise a number differing from the number of individual elements and/or components and/or units and/or method steps mentioned here, and/or any desired expedient combination thereof. Furthermore, for the value ranges specified in this disclosure, values lying within the limits mentioned also apply as disclosed and usable as desired.

DRAWINGS

Further advantages may be found in the following description of the drawings. Exemplary embodiments of the invention are represented in the drawings. The drawings, the description and the claims contain numerous features in combination. The person skilled in the art will expediently also consider the features individually and combine them to form other useful combinations.

Figure 2:
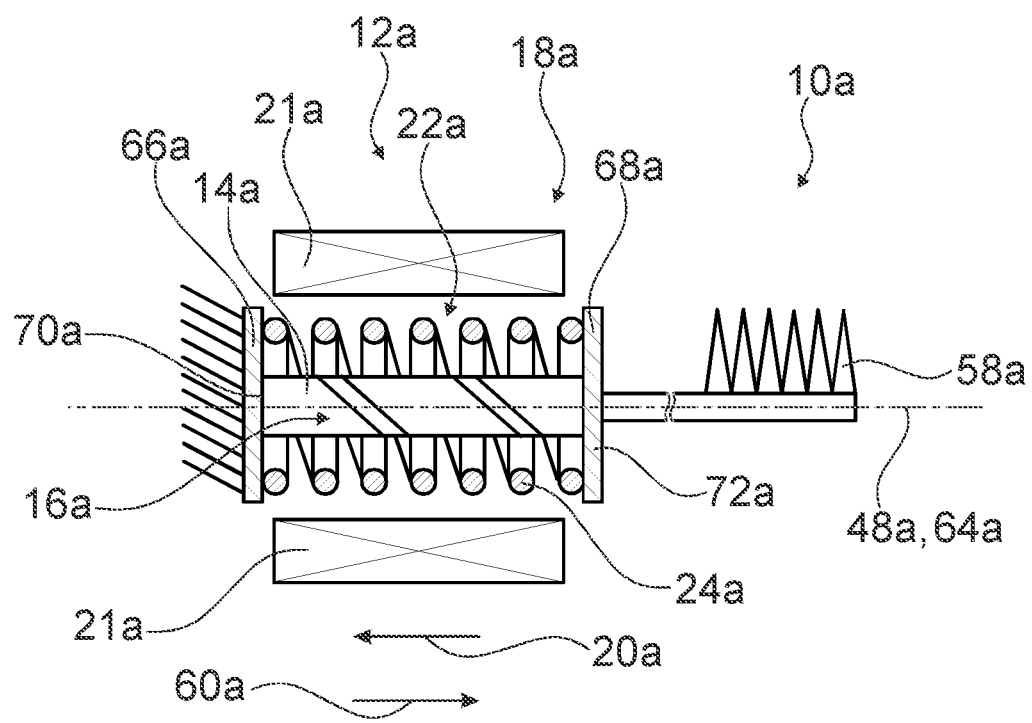
Figure 3A:
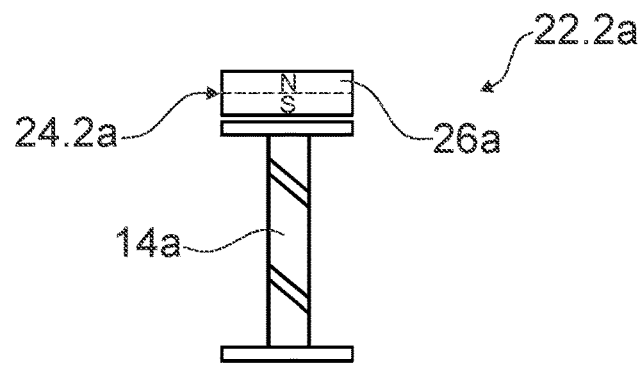
Figure 3B:
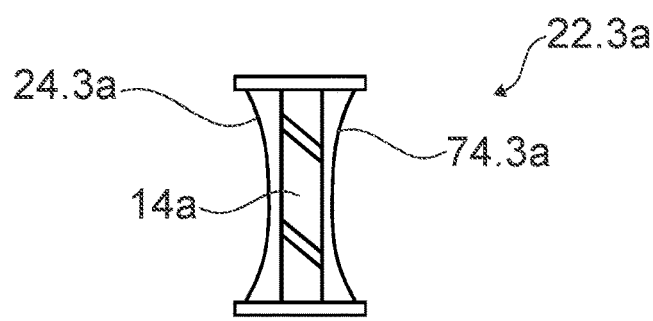
Figure 3C:
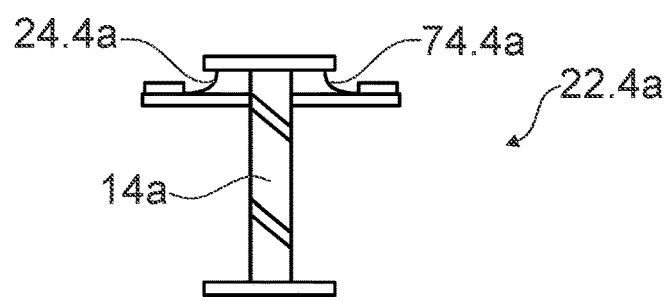
Figure 3D:
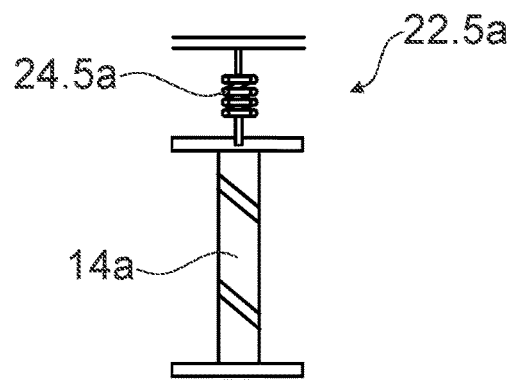
Figure 4:
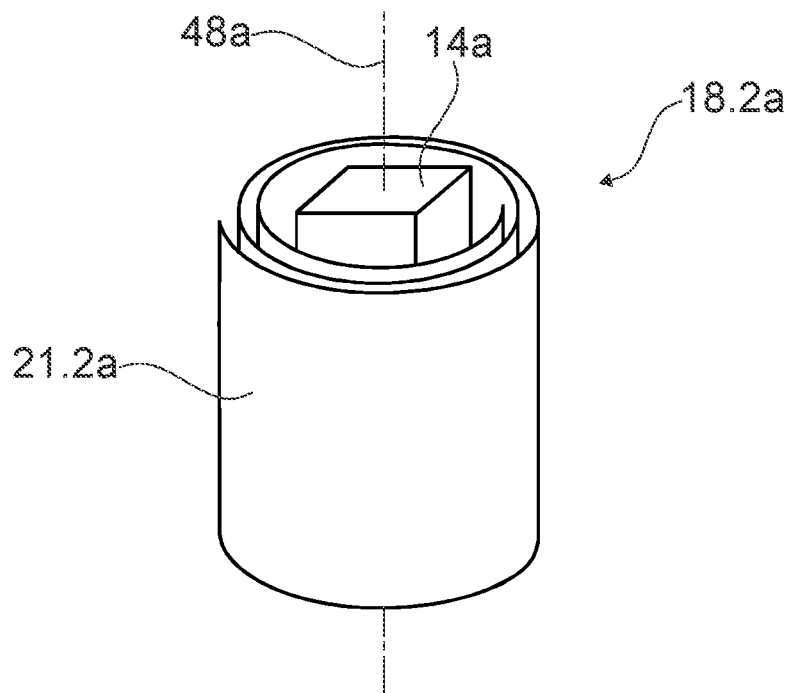
Figure 5:
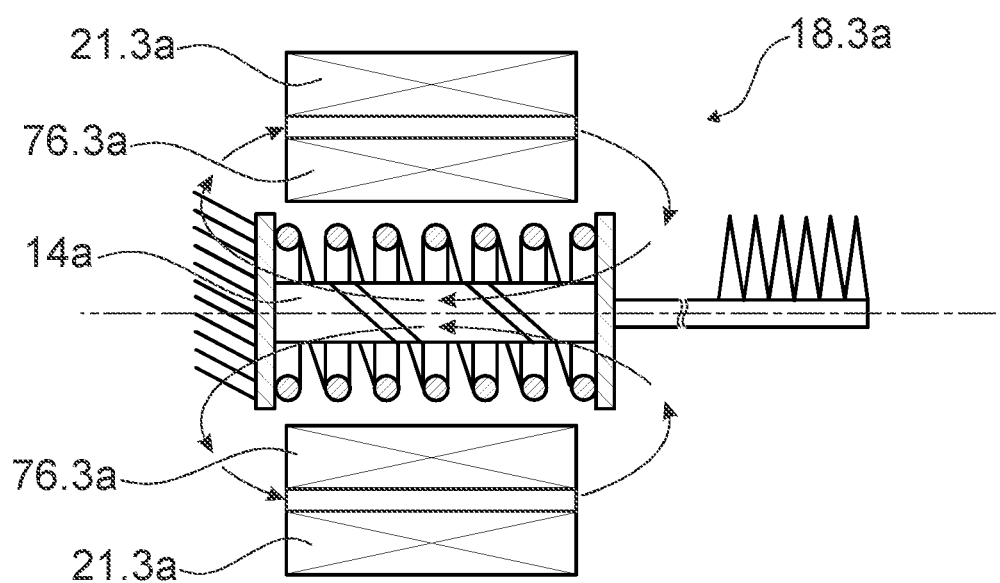
Figure 6:
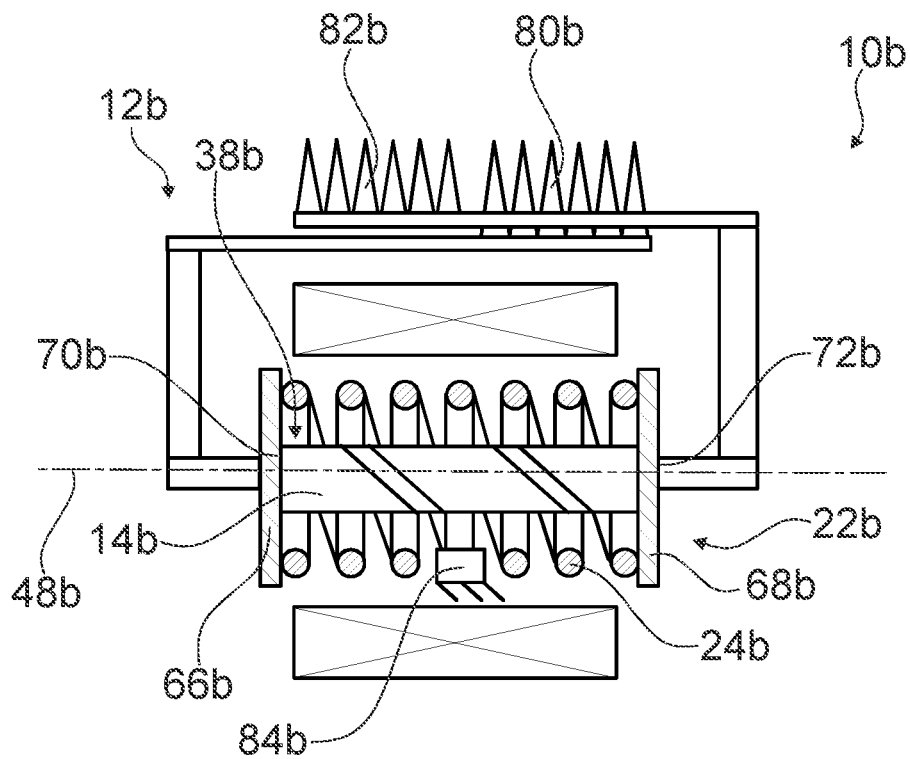
Figure 7:
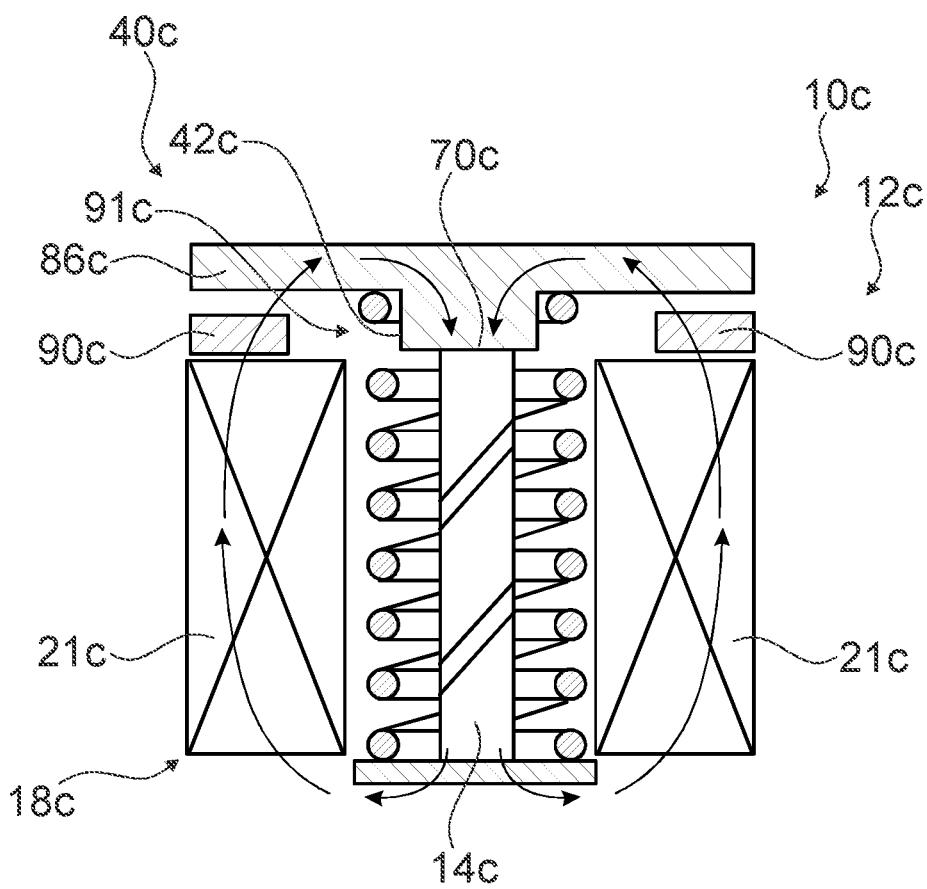
Figure 8:
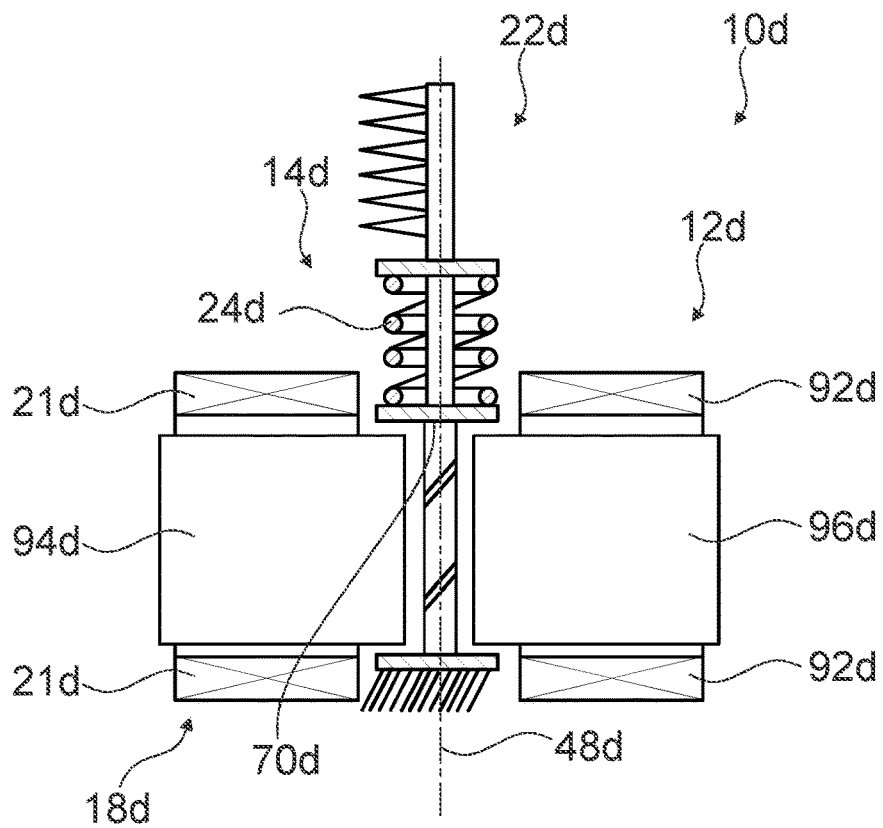
Figure 9:
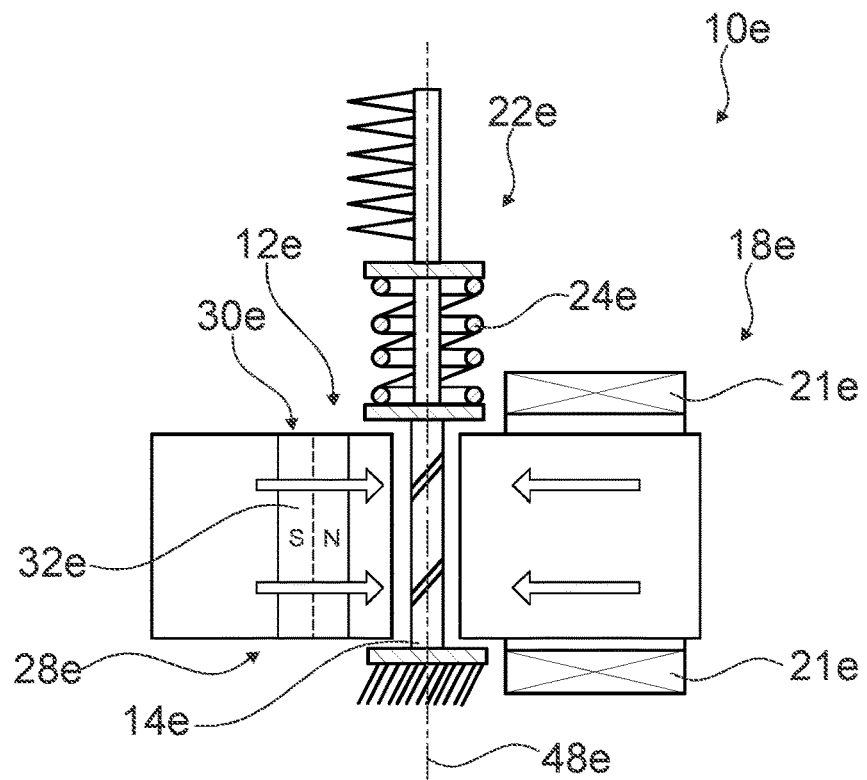
Figure 10:
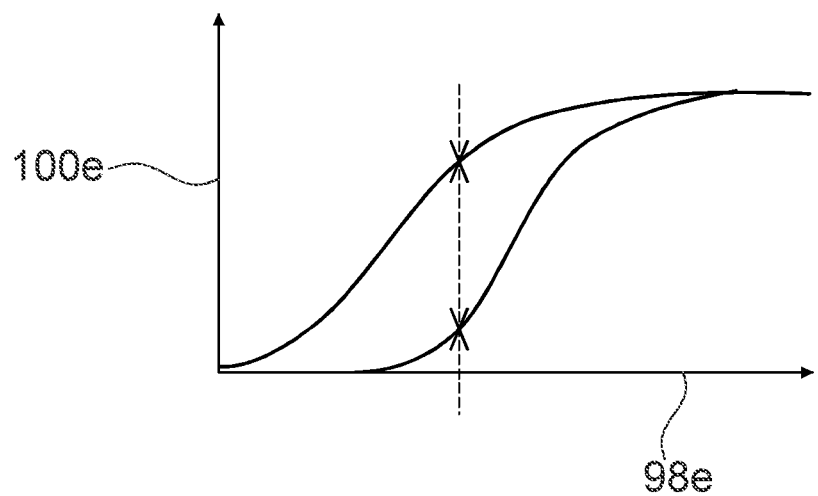
Figure 11:
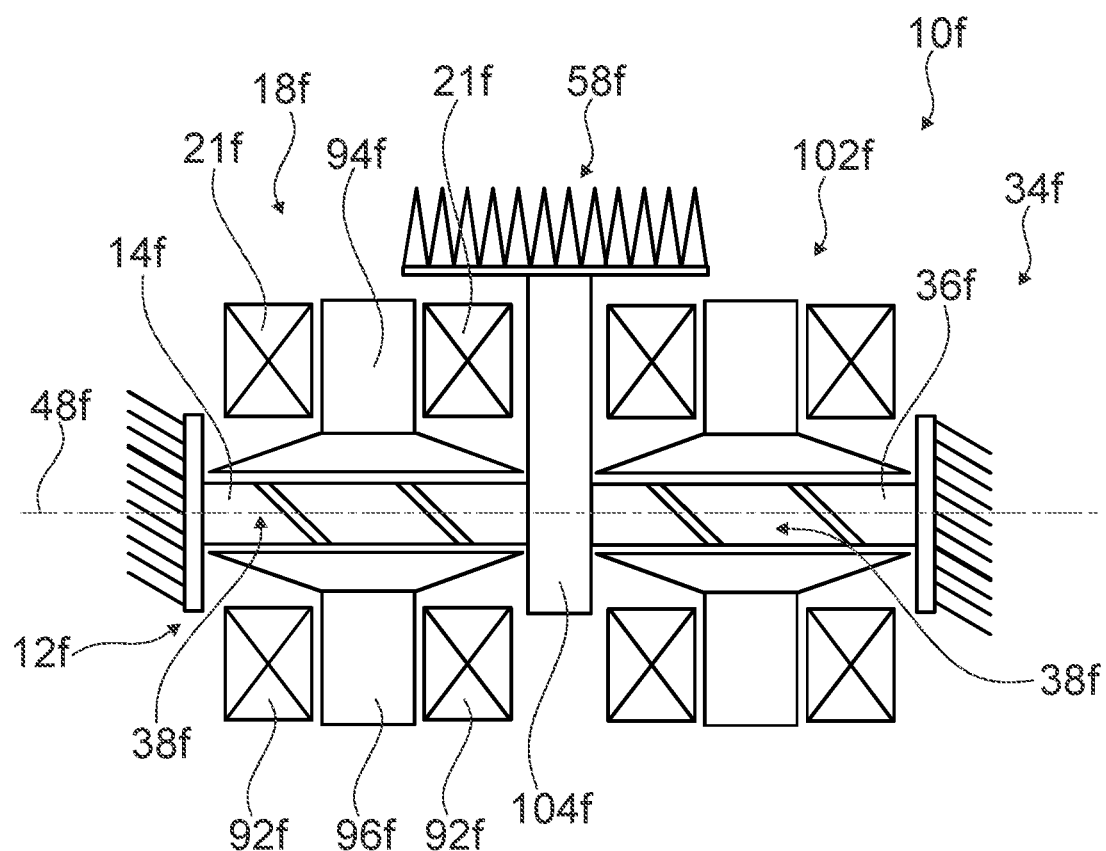
Figure 12:
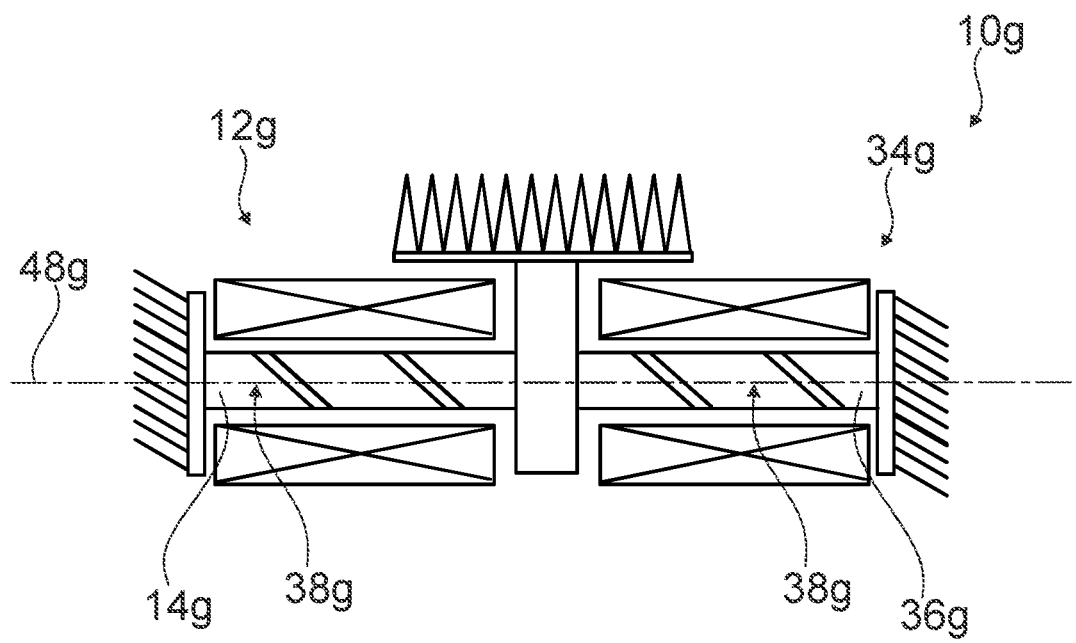
Figure 13:
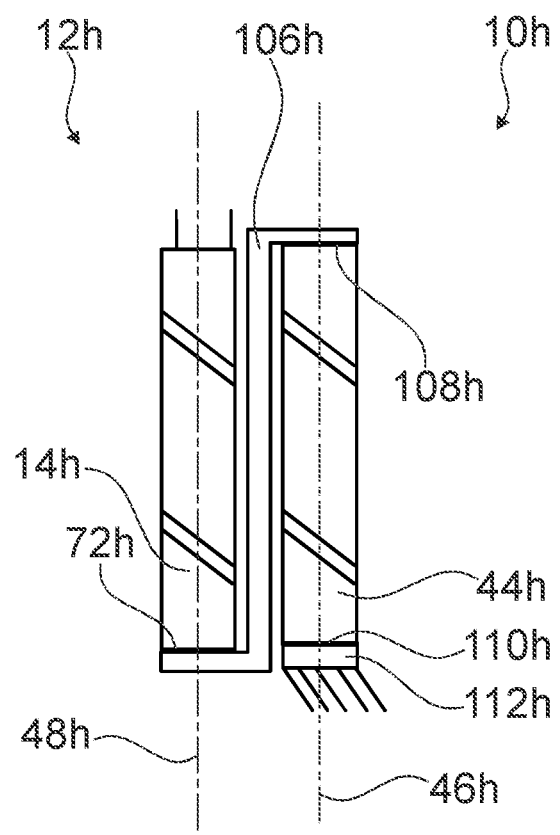
Figure 14:
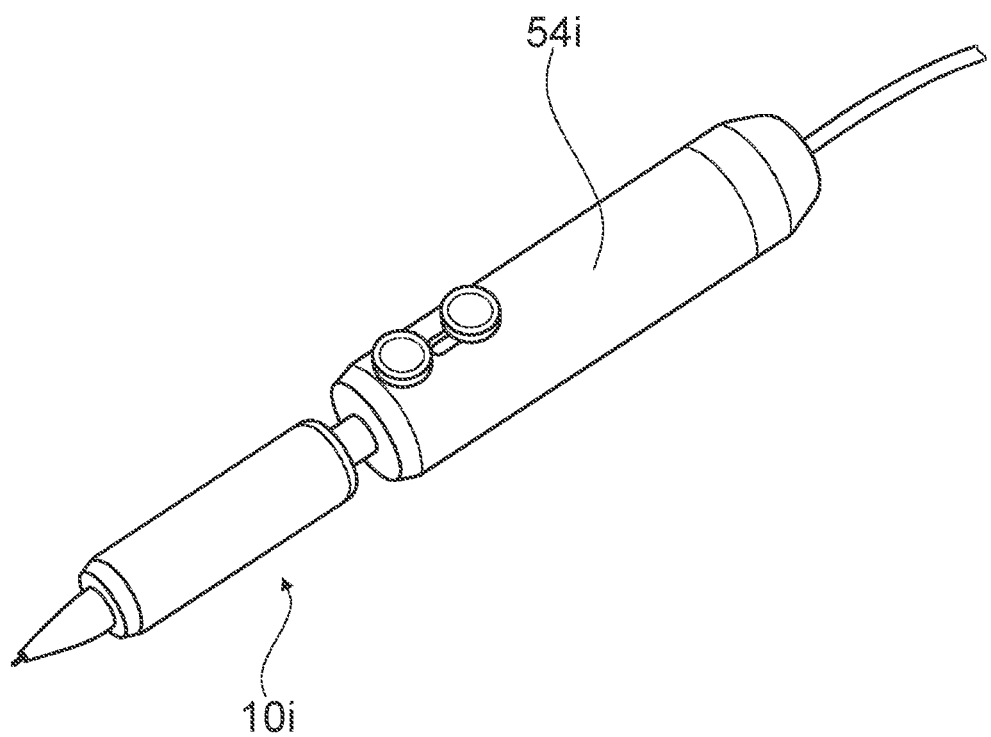
Figure 15:
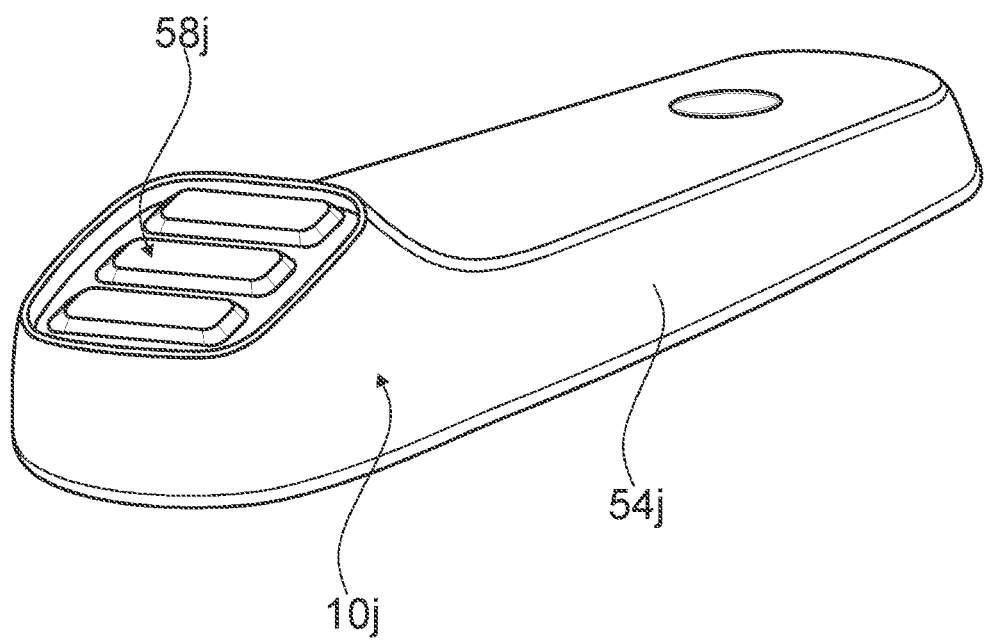
Figure 16:
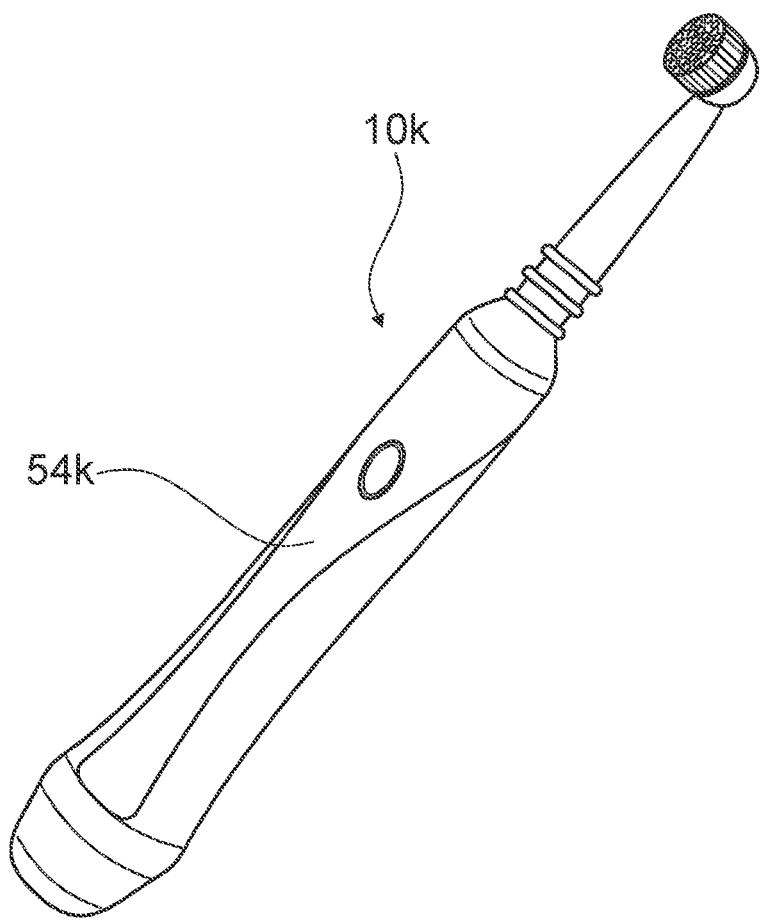

FIG. 1 shows a small appliance having a small appliance device in a schematic plan view, FIG. 2 shows a part of the small appliance device with a drive unit of the small appliance device in a schematic sectional representation, FIG. 3 shows schematic representations of alternative reset units for the drive unit, FIG. 4 shows a first alternative magnet unit for the drive unit in a perspective representation, FIG. 5 shows a second alternative magnet unit for the drive unit in a schematic sectional representation, FIG. 6 shows a first alternative small appliance device in a schematic sectional representation, FIG. 7 shows a second alternative small appliance device in a schematic sectional representation, FIG. 8 shows a third alternative small appliance device in a schematic sectional representation, FIG. 9 shows a fourth alternative small appliance device in a schematic sectional representation, FIG. 10 shows a schematic magnetic field/expansion diagram of a drive element of the fourth alternative small appliance device, FIG. 11 shows a fifth alternative small appliance device in a schematic sectional representation, FIG. 12 shows a sixth alternative small appliance device in a schematic sectional representation, FIG. 13 shows a part of a seventh alternative small appliance device in a schematic representation, FIG. 14 shows a first alternative small appliance in a perspective representation, FIG. 15 shows a second alternative small appliance in a perspective representation, and FIG. 16 shows a third alternative small appliance in a perspective representation.

DESCRIPTION OF THE EXEMPLARY EMBODIMENTS

FIG. 1 shows a small appliance 54a having a small appliance device 10a in a schematic plan view. In the present case, the small appliance 54a is embodied as a shaver. The small appliance 54a could, however, be implemented as any other desired body-care small appliance and/or body-treatment small appliance. For example, the small appliance 54a may be a beard trimmer, a hair trimmer, an epilating appliance, a tattooing appliance, a pricking appliance, a piercing appliance, an electric toothbrush or the like. It is furthermore conceivable for the small appliance 54a to be a combined device which comprises functions of a plurality of devices. The small appliance device 10a is in the present case embodied as a shaving apparatus device, but could also be implemented in any other desired way in a similar way to the small appliance 54a. In particular, the small appliance device 10a may be any desired small electric appliance and/or household small appliance device and/or household small electric appliance.

The small appliance 54a and/or the small appliance device 10a may be used for body care and/or body treatment. Furthermore, a method in which at least one body-care activity and/or at least one body treatment is carried out, may be carried out with the small appliance 54a and/or with the small appliance device 10a.

The small appliance device 10a comprises an energy supply unit 50a having at least one energy store 52a. In the present case, the energy store 52a is embodied as a battery, in particular as a lithium-ion battery. The energy store 52a could as an alternative also comprise and/or be implemented as at least one supercapacitor, at least one lithium polymer battery, at least one capacitor or any other desired energy storage element. Furthermore, in the present case the energy supply unit 50a comprises at least one interface 56a for connection to a supply network, in particular for charging the energy store 52a. As an alternative or in addition, it is conceivable for the small appliance device 10a to be supplied with energy directly by the interface 56a. In particular, the small appliance 54a may be implemented as a battery-operated small appliance or as a cabled small appliance.

The small appliance device 10a comprises at least one working tool 58a. In the present case, the working tool 58a is implemented as a combination of shaving blades. Depending on an implementation of the small appliance device 10a, however, any other desired working tools may of course be envisioned, such as blades, brush heads, tweezers, needles or the like.

FIG. 2 shows a part of the small appliance device 10a in a schematic sectional representation. The small appliance device 10a comprises a drive unit 12a. The drive unit 12a is configured to drive the working tool 58a. The drive unit 12a is configured to generate at least one drive movement, and advantageously to transmit this to the working tool 58a. The working tool 58a and its connection to the drive unit 12a are in this case represented only schematically in FIG. 2. In particular, a movement of the working tool 58a may be deviated and/or geared in comparison with a directly generated movement of the drive unit 12a, in particular by using at least one corresponding gearing, at least one force converter, at least one transmission element and the like. In the present case, for example, the drive unit 12a is configured to drive one shaving blade of the working tool 58a while a further shaving blade of the working tool 58a remains at rest, for example relative to a housing, so that the shaving blades move relative to one another. Of course, it is also conceivable for the drive unit 12a to move a plurality of shaving blades, particularly in opposite directions, relative to a housing and/or relative to one another.

In the present case, the drive unit 12a is configured to generate a repetitive and/or pulsed and/or pulse-like drive movement. Preferably, the drive unit 12a is configured, as a function of at least one operating state, in particular selectable by a user, to generate different drive movements which for example differ in respect of a repetition rate and/or an amplitude and/or a pulsed pattern or the like. In the present case, for example, a drive force and/or a movement speed of the shaving blades of the working tool 58a and/or the amplitude may be selected by a user. It is also conceivable for the drive unit 12a to be operable in a single-pulse mode in which, in particular, a single cutting movement may be initiated by the user, for example by pressing a button. In addition, arbitrary repetition rates for the drive movement may be envisioned, in particular even very slow repetition rates such as for example less than 100 Hz, less than 50 Hz, less than 20 Hz or even less than 10 Hz. Furthermore, even repetition rates of less than 1 Hz may be envisioned. In this case, a single-pulse power and/or a single-pulse energy is advantageously independent of the repetition rate.

The drive unit 12a comprises at least one drive element 14a. The drive element 14a comprises at least one magnetically shape-shiftable material 16a. The drive element 14a is implemented as a magnetically shape-shiftable drive element. The drive element 14a is implemented in the shape of a pin. In the present case, the drive element 14a has an at least substantially rectangular or square cross section. In particular, the drive element 14a has a constant cross section along its longitudinal axis 48a. Furthermore, in the present case the drive element 14a is implemented as a solid body. However, other geometries of the drive element 14a may of course be envisioned. For example, it may be implemented cylindrically. Furthermore, the drive element 14a may be implemented at least section-wise as a hollow body.

The drive element 14a is configured to generate an actuation movement in at least one actuation direction 20a by at least one magnetically induced shape shift. The actuation movement may in this case correspond to the drive movement or be converted into it, for example by using an aforementioned conversion and/or gearing. The actuation movement corresponds in the present case to a length change of the drive element 14a along its longitudinal axis 48a. In particular, the actuation direction 20a is arranged parallel to the longitudinal axis 48a of the drive element 14a. The longitudinal axis 48a of the drive element 14a is arranged parallel to its main extent direction 60a.

The magnetically shape-shiftable material 16a is a magnetic shape-memory material. In particular, the magnetically shape-shiftable material 16a is a magnetic shape-memory alloy. In principle, however, it is likewise conceivable for the magnetically shape-shiftable material 16a to be a magnetostrictive material. The magnetically shape-shiftable material 16a is monocrystalline in the present case. In particular, the drive element 14a is formed as a single crystal from the magnetically shape-shiftable material 38a.

The magnetically shape-shiftable material 16a contains nickel, manganese and gallium. In particular the magnetically shape-shiftable material 16a is a nickel-manganese-gallium shape-memory alloy. In the present case, the magnetically shape-shiftable material 16a comprises between 45% and 55% nickel, between 20% and 30% manganese and between 20% and 30% gallium, expressed in terms of weight, although, as mentioned above, other compositions may also be envisioned in principle.

The drive unit 12a comprises a magnet unit 18a, which is configured to generate at least one time-variable shape-shiftable magnetic field for the drive element 14a. The shape-shiftable magnetic field is applied in the event of actuation to the drive element 14a. The shape-shiftable magnetic field causes a magnetic shape shift of the drive element 14a. In particular, the magnet unit 18a is drivable, for example by means of electrical pulses. In the present case, the small appliance device 10a comprises a control and regulating unit (not shown) which is configured to drive the magnet unit 18a, for example as a function of an operating state, in particular selectable by a user. Furthermore, the control and regulating unit is configured to regulate an actuation movement generated by the drive element 14a, for example as a function of a setpoint value/actual value comparison of a position and/or of a speed and/or of a counter-force of the working tool 58a, for instance in order to achieve a constant actuation speed or a constant actuation force or a particular target characteristic curve, or the like.

The magnet unit 18a comprises at least one coil element 21a. The coil element 21a is embodied as a wire coil. The coil element 21a encompasses the drive element 14a at least partially. In the present case, the coil element 21a fully encompasses the drive element 14a and/or its longitudinal axis 48a as seen along the longitudinal axis 48a of the drive element 14a. A coil axis 64a of the coil element 21a corresponds to the longitudinal axis 48a of the drive element 14a. The coil element 21a is wound in such a way that its turns extend around the drive element 14a. The drive element 14a is arranged inside the coil element 21a. The coil element 21a is configured to generate the shape-shiftable magnetic field. In the present case, field lines of the shape-shiftable magnetic field extend at least substantially parallel to the longitudinal axis 48a of the drive element 14a in a region of the drive element 14a, in particular inside the drive element 14a.

The magnet unit 18a is configured to initiate a contraction of the drive element 14a parallel to the actuation direction 20a. In the present case, the drive element 14a shortens in reaction to a field pulse of the shape-shiftable magnetic field which passes through the drive element 14a in particular parallel to its longitudinal axis 48a. A field pulse of the shape-shiftable magnetic field is generated by means of brief energizing, advantageously for at most 10 ms, particularly advantageously for at most 5 ms and preferably for at most 2 ms, or for even shorter times, of the coil element 21a. Of course, for generation of a contracting shape-shiftable magnetic field, it is likewise conceivable for the drive element 14a to be arranged outside the coil element 21a and for the magnet unit 18a to comprise correspondingly implemented magnet guiding elements. Particularly in this case, it is conceivable for the magnet unit 18a to comprise a plurality of coil elements 21a, which in particular may be implemented at least substantially identically or differently and/or connected in parallel and/or in series.

The small appliance device 10a comprises a reset unit 22a, which is configured to apply a reset force to the drive element 14a. In particular, the reset force is configured for reverse deformation of the drive element 14a. The reset unit 22a is configured to counteract a contraction of the drive element 14a parallel to the actuation direction 20a. During operation of the small appliance device 10a, the drive element 14a is repeatedly deformed, in particular shortened, and reversely deformed, in particular expanded, particularly in each case along its longitudinal axis 48a. In the absence of a shape-shiftable magnetic field, the reset force in the present case generates a further actuation movement in a direction opposite to the actuation direction 20a. The drive unit 12a therefore generates a to-and-fro movement, the amplitude, repetition rate, speed and/or acceleration of which can be adjusted by suitable selection of a time profile of the shape-shiftable magnetic field, in particular suitable field pulses.

The reset unit 22a comprises at least one reset element 24a. The reset element 24a may, for example, be embodied as a mechanical spring. In the case shown, the reset element 24a is implemented for instance as a compression spring, in particular as a helical spring. The drive element 14a is arranged inside the reset element 24a. The reset element 24a is connected to a first support element 66a and to a second support element 68a. Support elements 66a, 68a are connected respectively to a front face 70a, 72a, in particular arranged perpendicularly to the longitudinal axis 48a of the drive element 14a, of the drive element 14a. In the present case, the first support element 66a is fixed to a housing, while during actuation of the drive element 14a the second support element 68a is moved by the actuation movement relative to a housing of the small appliance 54a. During actuation, the drive element 14a is shortened counter to the reset force along its longitudinal axis 48a. Upon the shape-shiftable magnetic field being turned off or at least having its field strength reduced, the reset element 24a extends the drive element 14a along its longitudinal axis 48a, so that it is reversely deformed.

Reference is again made below to FIG. 1. The small appliance device 10a in the present case comprises a control and/or regulating unit 78a. The small appliance device 10a furthermore comprises an operating unit 81a, which is configured for input of user commands. For example, the operating unit 81a may comprise an on and/or off switch and advantageously at least one selector switch for selecting operating modes. It is also conceivable for the operating unit 81a to comprise a display, in particular a touch display, and/or another input and/or output means for input and/or output of information, for example status information, charging status information, operating status information, a time of day, an application plan, a treatment plan or the like, and/or commands and/or at least one selection or the like. It is furthermore conceivable for the small appliance device 10a to comprise at least one data interface, in particular for a wireless data connection, which is configured in particular for connection to an external database. For example, operating parameters for not yet stored additional operating states may be retrieved via such a data interface. In particular, it is conceivable for a user to be offered by means of the operating unit 81a a connection to the external database, for example to extend an operating mode range. This may, for example, relate to special operating modes of the external database, which make it possible to adapt operating modes to particular application parameters, for example a hair color, a hair thickness, a hair length, a skin color, and age and/or a sex of the user, or of a patient and/or customer and/or treatment recipient and/or application recipient or the like. Advantageously, the operating unit 81a is connected to the control and/or regulating unit 78a. The control and/or regulating unit 78a is configured to drive the magnet unit 18a, in particular as a function of a selected operating mode. Furthermore, in the present case the control and/or regulating unit 78a is configured to regulate a movement of the working tool 58a. For example, a current through the coil element 21a for generating the shape-shiftable magnetic field and/or its time profile may be regulated in this way.

FIG. 3 shows schematic representations of alternative reset units 22.2a-22.5a for the drive unit 12a. The concepts disclosed in connection with FIG. 3 may be used instead of the reset unit 22a shown in FIG. 2. Furthermore, in a similar way, reset units may be envisioned which, instead of a compressive force that leads to a reset of the drive element 14a, generate a tensile force and/or suitable torsion forces and/or shear forces. Furthermore, any desired combinations may be envisioned, for example of different reset elements, for instance in order to deliberately influence a spring characteristic curve.

The reset unit 22.2a of FIG. 3a comprises, as a reset element 24.2a, a magnetic spring (only represented schematically in the figure). The reset unit 22a comprises at least one magnet element 26a in the example of FIG. 3. The magnet element 26a is in the present case implemented as a permanent magnet. The magnet element 26a is a part of the reset element 24.2a. For reasons of clarity, only one magnet element 26a is represented in FIG. 3a. It is, however, conceivable for the reset element 24.2a to comprise a multiplicity of magnet elements 26a, which form a part of a magnetic spring. In this case, it is conceivable for at least some magnet elements 26a to be implemented as electromagnets so that, for example, a variable spring characteristic curve may be achieved. The reset element 24.2a may in principle be implemented in such a way that it has a nonlinear spring characteristic curve. In the present case, the reset element 24.2a has a degressive spring characteristic curve, so that more energy can be stored in the spring extension in comparison with a linear spring characteristic curve. The reset element 24.2a may be implemented as any desired magnetic spring and, for example, be arranged on at least one front face 70a, 72a of the drive element 14a. It is likewise conceivable for the reset element 24.2a to encompass the drive element 14a at least partially or fully, in particular as seen along the longitudinal axis 48a of the drive element 14a (cf. FIG. 2).

The reset units 22.3a, 22.4a of FIGS. 3b and 3c comprise reset elements 24.3a, 74.3a, 24.4a, 74.4a which are implemented as curved elements, for example as leaf springs and/or as curved spring wires or the like. Depending on an implementation and extension state of the drive element 14a, they may apply a tensile force or a compressive force to the drive element 14a.

The reset unit 22.5a of FIG. 3d comprises a reset element 24.5a which is arranged on a front face 72a of the drive element 14a. In particular, in the present case the drive element 14a is arranged outside the reset element 24.5a. The reset element 24.5a may, for example, be implemented as a tension spring. In the arrangement shown, a reset tensile force for the drive element 14a may be generated by means of the reset element 24.5a. In principle, it is similarly conceivable to generate a reset compressive force by means of a compression spring.

FIG. 4 shows a first alternative magnet unit 18.2a for the drive unit 12a in a perspective representation. The first alternative magnet unit 18.2a comprises a first alternative coil element 21.2a. The first alternative coil element 21.2a is implemented as a tape coil. The first alternative coil element 21.2a encompasses the drive element 14a at least partially. As seen along the longitudinal axis 48a of the drive element 14a, the first alternative coil element 21.2a encompasses the drive element 14a fully.

FIG. 5 shows a second alternative magnet unit 18.3a for the drive unit 12a in a schematic sectional representation. The second alternative magnet unit 18.3a comprises a first coil element 21.3a. The second alternative magnet unit 18.3a furthermore comprises a second coil element 76.3a. The coil elements 21.3a, 76.3a of the second alternative magnet unit 18.3a are arranged concentrically, coil axes of the coil elements 21.3a, 76.3a corresponding in particular to the longitudinal axis 48a of the drive element 14a. The coil elements 21.3a, 76.3a of the second alternative magnet unit 18.3a are in the present case electrically connected in parallel, so that in particular a low overall resistance may be achieved.

FIGS. 6 to 16 show further exemplary embodiments of the invention. The description below is restricted essentially to the differences between the exemplary embodiments, in which case in relation to components, features and functions that remain the same, reference may be made to the description of the other exemplary embodiments, in particular the exemplary embodiment of FIGS. 1 to 5. In order to distinguish between the exemplary embodiments, the letter a in the references of the exemplary embodiment in FIG. 1 is replaced with the letters b to k in the references of the exemplary embodiments of FIGS. 6 to 16. In relation to components that are denoted identically, particularly in relation to components having the same references, reference may also be made in principle to the drawings and/or the description of the exemplary embodiment of FIGS. 1 to 6.

FIG. 6 shows a first alternative small appliance device 10b in a schematic sectional representation. The first alternative small appliance device 10b comprises a drive unit 12b which is constructed in substantially the same way as the drive unit 12a of FIGS. 1 to 5. The drive unit 12b comprises a drive element 14b, which shortens along its longitudinal axis 48b during operation. The drive element 14b is formed from a magnetically shape-shiftable material 38b, in particular from a magnetic shape-memory alloy. The first alternative small appliance device 10b comprises at least one reset unit 22b having a reset element 24b that applies a reset force to the drive element 14b. The reset element 24b is implemented as a helical spring. The drive element 14b is arranged inside the reset element 24b in the present case.

The reset unit 22b in the present case comprises two support elements 66b, 68b, which are connected to opposite-situated front faces 70b, 72b of the drive element 14b. The support elements 66b, 68b are respectively connected to a shaving blade 80b, 82b of a working tool 58b of the first alternative small appliance device 10b, wherein the connection shown is to be understood purely schematically, and suitable lever elements, gear elements, eccentrics, force transmission elements and the like may of course be used. Furthermore, in particular with a corresponding implementation of the first alternative small appliance device 10b, components of a differently implemented working tool, for example of an epilation working tool, instead of the shaving blades 80b, 82b, may be connected to the support elements 66b, 68b. Furthermore, the support elements 66b, 68b are connected to the reset unit 22b, in particular to the reset element 24b. The reset unit 22b comprises a fastening element 84b, which forms a bearing that is stationary with respect to a housing. The fastening element 84b is connected to the reset element 24b. The drive element 14b is therefore supported by the fastening element 84b in such a way that its two front faces 70b, 72b, move relative to one another and relative to a housing of the first alternative small appliance device 10b during actuation. In this case, it is conceivable for a movement of the front faces 70b, 72b to be converted directly into a movement of the shaving blades 80b, 82b.

For a support of a drive element according to the invention, any desired variants may in principle be envisioned. For example, similarly as in the case of the first alternative small appliance device 10b, components of a working tool may be connected to front faces of the drive element, although one component is fixed to a housing so that the drive element is supported by means of a connection to the working tool. In addition, it is conceivable for a drive element to be connected by means of a single plunger or a single tension element to a working tool, in such a way that its components move relative to a housing and/or relative to one another. It is furthermore conceivable for the working tool to form a part of a reset unit, in which case, for example, a reset force may be transmitted by means of a connecting mechanism from the working tool to the drive element.

FIG. 7 shows a second alternative small appliance device 10c in a schematic sectional representation. The second alternative small appliance device 10c comprises a drive unit 12c having at least one drive element 14c. The drive element 14c is a magnetically shape-shiftable drive element. In addition, the second alternative small appliance device 10c comprises a magnet unit 18c having a coil element 21c. The drive unit 12c is configured to generate a drive force and/or a drive movement. Furthermore, the second alternative small appliance device 10c comprises a reluctance unit 40c, which is configured to generate an assisting drive force and/or an assisting drive movement. The reluctance unit 40c is configured to generate the assisting drive force and/or the assisting drive movement by using the reluctance principle. In the present case, a force generated by a compression of the drive element 14c along its longitudinal axis 48c is supplemented by the assisting drive force.

The reluctance unit 40c comprises an armature 86c made of a ferromagnetic material. The armature 86c is in the present case embodied in a one-part implementation with a support element 42c of the drive unit 12c. The support element 42c is at least partially embodied in a one-part implementation with the reluctance unit 40c. The support element 42c is connected to a front face 70c of the drive element 14c.

The reluctance unit 40c in the present case furthermore comprises a yoke 90c. The yoke 90c is, for example, implemented in the shape of a ring. Furthermore, the yoke 90c is connected to the coil element 21c. Arranged between the yoke 90c and the support element 42c, there is a distance 91c, which in the present case is likewise ring-shaped. An inner radius of the yoke 90c is in this case substantially greater than an outer radius of the support element 42c, so that a magnetic flux generated by the coil element 21c can be guided through the yoke 90c and the armature 86c into the drive element 14c and not predominantly from the yoke 90c directly into the drive element 14c. If a shape-shiftable magnetic field is generated by means of the coil element 21c, the armature 86c is moved in a direction toward the yoke 90c and therefore assists a movement generated by the drive element 14c. The drive unit 12c in the present case comprises the reluctance unit 40c. The drive unit 12c is embodied as an MSM-reluctance hybrid drive unit.

While in the present case a contraction of the drive element 14c is assisted by means of the reluctance unit 40c, by corresponding arrangement of component parts and use of flux guiding means it is likewise conceivable for an expansion of a drive unit to be assisted.

FIG. 8 shows a third alternative small appliance device 10d in a schematic sectional representation. The fourth alternative small appliance device 10d comprises a drive unit 12d having at least one drive element 14d. The drive element 14d is formed from a magnetic shape-memory alloy. Furthermore, the third alternative small appliance device 10d comprises a magnet unit 18d having at least one coil element 21d, 92d. In the present case, the magnet unit 18d comprises a first coil element 21d and a second coil element 92d. The coil elements 21d, 92d are arranged on opposite long sides of the drive element 14d. The magnet unit 18d comprises a first flux guiding element 94d and a second flux guiding element 96d, each being made of a ferromagnetic material, for example. If, for example by means of pulsed energizing, a shape-shiftable magnetic field is generated by means of the coil elements 21d, 92d, its flux is guided to the drive element 14d in such a way that magnetic field lines can pass through the latter substantially perpendicularly to its longitudinal axis 48d. The shape-shiftable magnetic field is in this case configured to cause an expansion of the drive element 14d along its longitudinal axis 48d.

The first alternative small appliance device 10d furthermore comprises a reset unit 22d having at least one reset element 24d. The reset element 24d generates a reset force, which acts on a front face 70d of the drive element 14d. The reset element 24d is arranged, as seen from the drive element 14d, in front of the front face 70d of the latter. The reset force is configured for reverse deformation of the drive element 14d. Particularly in the absence of the shape-shiftable magnetic field, the reset force causes a shortening of the drive element 14d along its longitudinal axis 48d. The reset element 24d is in the present case embodied as a compression spring, which presses against the front face 70d of the drive element 14d.

FIG. 9 shows a fourth alternative small appliance device 10e in a schematic sectional representation. The fourth alternative small appliance device 10e comprises a drive unit 12e having at least one drive element 14e. The drive element 14e is in the present case implemented as a magnetically shape-shiftable drive element. The fourth alternative small appliance device 10e comprises a magnet unit 18e having at least one coil element 21e generating a shape-shiftable magnetic field for the drive element 14e. The shape-shiftable magnetic field is configured to cause an expansion of the drive element 14e along its longitudinal axis 48e. In particular, field lines of the shape-shiftable magnetic field in the region of the drive element 14e extend at least substantially perpendicularly to its longitudinal axis 48e.

The drive element 14e can be brought into at least one first stable expansion state and into at least one second stable expansion state. The expansion states are respectively characterized by a defined length of the drive element 14e parallel to its longitudinal axis 48e. In particular, the first stable expansion state and the second stable expansion state differ from a maximum and/or a minimum expansion state of the drive element 14e. In particular, the stable expansion states are stable to the extent that, in the absence of energizing of the magnet unit 18e, the drive element 14e maintains a length corresponding to the respective expansion state along its longitudinal axis 48e, no energy advantageously being consumed.

The fourth alternative small appliance device 10e comprises a holding unit 28e, which is configured to stabilize the first stable expansion state and the second stable expansion state. The holding unit 28e is configured to superimpose a holding magnetic field on the shape-shiftable magnetic field. Furthermore, the holding unit 28e is configured to pre-stress the drive element 14e. The holding unit 28e is at least partially embodied in a one-part implementation with a reset unit 22e of the fourth alternative small appliance device 10e, which comprises at least one reset element 24e. The reset element 24d pre-stresses the drive element 14e. In particular, the reset element 24d applies a compressive force to the drive element 14e. It is, however, likewise conceivable for a tensile force to be applied to the drive element 14e, in particular if the shape-shiftable magnetic field is applied in such a way that it causes shortening of the drive element 14e along its longitudinal axis 48e.

In the present case, the holding unit 28e comprises at least one holding magnet element 30e. The holding magnet element 30e may for example comprise and/or be implemented as at least one permanent magnet, which particularly during operation of the fourth alternative small appliance device 10e is not magnetically reversible. To this end, for example, an NdFeB- and/or SmCo-based rare-earth magnet could be used. By using the superimposed magnetic field of the holding magnet element 30e and the prestress of the drive element 14e, a hysteresis of the material of the drive element 14e may be used in such a way that the first stable expansion state and the second stable expansion state can be achieved. This is represented in FIG. 10, which shows a schematic magnetic field/expansion diagram of the drive element 14e. The magnetic field/expansion diagram has a magnetic field strength axis 98e and an expansion state axis 100e. The marked points denote two different stable expansion states of the drive element 14e. These are present in a common magnetic field which corresponds to an absence of the shape-shiftable magnetic field and is generated only by the holding magnet element 30e. It is possible to switch between the expansion states by energizing the coil element 21e, a length of the drive element 14e subsequently remaining in the absence of current at a correspondingly fixed value.

In the present case, the holding element 30e comprises and/or is implemented as at least one magnetically reversible permanent magnet 32e. In the present case, the magnetically reversible permanent magnet 32e is, for example, an AlNiCo Magnet. In contrast to the described case of a permanent magnet that is not magnetically reversible, a magnetization of the magnetically reversible permanent magnet 32e is modified by the shape-shiftable magnetic field. During operation of the drive unit 12e and of the magnet unit 18e, the magnetically reversible permanent magnet 32e is deliberately magnetized and demagnetized.

FIG. 11 shows a fifth alternative small appliance device 10f in a schematic sectional representation. The fifth alternative small appliance device 10f comprises a drive unit 12f having at least one drive element 14f. The drive element 14f is formed from a magnetically shape-shiftable material 38f. The drive unit 12f is configured to generate an actuation movement by means of expansion of the drive element 14f. The fifth alternative small appliance device 10f comprises a magnet unit 18f having two coil elements 21f, 92f as well as suitable flux guiding elements 94f, 96f. The magnet unit 18f is configured to generate a shape-shiftable magnetic field for the drive element 14f, which passes through the drive element 14f at least substantially perpendicularly to its longitudinal axis 48f.

The fifth alternative small appliance device 10f comprises a second drive unit 34f. The second drive unit 34f is arranged antagonistically with respect to the drive unit 12f. The second drive unit 34f comprises at least one second drive element 36f. The second drive element 36f comprises at least one magnetically shape-shiftable material 38f. In the present case, the second drive element 36f is formed as a magnetically shape-shiftable element. The drive element 14f and the second drive element 36f are implemented at least substantially identically to one another. The drive element 14f and the second drive element 36f are arranged opposite one another. In particular, the drive element 14f and the second drive element 36f have a common longitudinal axis 48f and/or are arranged flush with respect to their longitudinal axes 48f. The fifth alternative small appliance device 10f furthermore comprises a second magnet unit 102f, which is configured to generate a shape-shiftable magnetic field for the second drive element 14f. The second magnet unit 102f is in the present case implemented at least substantially identically and/or mirror-symmetrically with respect to the magnet unit 18f. The drive element 14f and the second drive element 36f are arranged in such a way that an expansion of one drive element 14f, 36f respectively causes a compression of the other drive element 36f, 14f. In particular, the second drive unit 34f forms a reset unit for the drive element 14f. Furthermore, the drive unit 12f forms a reset unit for the second drive element 36f. Furthermore, the drive units 12f, 34f together form a holding unit for the drive element 14f and the second drive element 36f, which is configured to stabilize respectively at least one first stable expansion state and at least one second stable expansion state of the drive element 14f and of the second drive element 36f. In the present case, the drive units 12f, 34f together form at least a part of a bistable MSM push-push actuator. In order to generate an actuation movement, one drive element 14f, 36f is respectively extended, while the other respective drive element 36f, 14f is shortened.

In the present case, the drive elements 14f, 36f are connected to at least one lever element 104f, which is tilted to and fro during actuation. Advantageously, the drive units 12f, 34f are connected to two lever elements 104f, which in particular are in turn connected to a working tool 58f of the fifth alternative small appliance device 10f (which is represented only schematically in FIG. 11). In a similar way to the cases described above, any desired implementation of a mechanism for movement transmission may of course be envisioned.

FIG. 12 shows a sixth alternative small appliance device 10g in a schematic sectional representation. The sixth alternative small appliance device 10g comprises a drive unit 12g having at least one drive element 14g made of a magnetically shape-shiftable material 38g. Furthermore, the sixth alternative small appliance device 10g comprises a second drive unit 34g having at least one second drive element 36g made of a magnetically shape-shiftable material 38g. The drive unit 12g and the second drive unit 34g are arranged antagonistically. In contrast to the exemplary embodiment of FIG. 11, in FIG. 12 the drive units 12g, 34g are respectively configured to provide an actuation movement by means of contraction of the drive elements 14g, 36g along their longitudinal axis 48g. In a similar way to FIG. 11, in FIG. 12 the drive elements 14g, 36g move in opposite directions and carry out mutual reset. The drive unit 12g and the second drive unit 34g in FIG. 12 together form at least a part of a bistable MSM pull-pull actuator.

FIG. 13 shows a part of a seventh alternative small appliance device 10h in a schematic representation. The seventh alternative small appliance device 10h comprises a drive unit 12h, which is partially represented in FIG. 13. The drive unit 12h comprises a drive element 14h made of a magnetically shape-shiftable material. The drive unit 12h furthermore comprises a further drive element 44h, which is connected in series with the drive element 14h in respect of a drive effect and the longitudinal axis 46h of which is different to a longitudinal axis 48h of the drive element 14h. The longitudinal axis 46h of the further drive element 44h and the longitudinal axis 48h of the drive element 14h are in the present case arranged at least substantially parallel to one another. The drive element 14h and the further drive element 44h, in particular their long sides, are arranged next to one another.

Of course, both for the case of a push-push actuator and for the case of a pull-pull actuator, it is respectively conceivable to configure at least one drive unit as a hybrid MSM-reluctance drive unit. Likewise, at least one drive unit may be implemented as any other desired drive unit, for example a linear drive unit, a reluctance drive unit, a piezo drive unit, a moving-coil drive unit and/or the like.

The drive unit 12h comprises a stroke transmission element 106h. The stroke transmission element 106h is configured to add a stroke generated by the drive element 14h and the further drive element 44h. The stroke transmission element 106h is in the present case implemented in the shape of a step. The stroke transmission element 106h is implemented in the shape of a Z. The stroke transmission element 106h connects a rear front face 72h of the drive element 14h to a front front face 108h of the further drive element 44h. In the present case, the stroke transmission element 106h is a sheet-metal part. The further drive element 44h is mounted fixed, in particular fixed to a housing, on a rear front face 110h, which in particular is opposite the front front face 108h along the longitudinal axis 46h of the further drive element 44h by means of a support element 112h. During a contraction or an expansion of the further drive element 44h, in particular parallel to its longitudinal axis 46h, the rear side 72h of the drive element 14h is moved relative to the support element 112h. If the drive element 14h is likewise contracted or expanded, the corresponding movements are added. Preferably, the drive element 14h and the further drive element 44h are arranged in a common magnetic field region, and/or a shape-shiftable magnetic field is provided for the drive element 14h and the further drive element 44h by means of a common magnet unit (not represented). The schematically represented concept of stroke addition may, of course, be used for an arbitrary number of drive elements in combination. Furthermore, use in a tensile as well as in a compressive configuration is conceivable.

FIG. 14 shows a first alternative small appliance 54i in a perspective representation. The first alternative small appliance 54i comprises at least one small appliance device 10i. The first alternative small appliance 54i is embodied as a tattooing appliance. The small appliance device 10i is embodied as a tattooing appliance device. The first alternative small appliance 54i and/or the small appliance device 10i may be used for body treatment.

FIG. 15 shows a second alternative small appliance 54j in a perspective representation. The second alternative small appliance 54j comprises at least one small appliance device 10j. The second alternative small appliance 54j is embodied as an epilating appliance. The small appliance device 10j is embodied as an epilating appliance device. The small appliance device 10j may comprise a working tool 58j which, in contrast to a conventional epilating drum operating in rotation, comprises linearly moved elements, for example tweezers, for hair removal. The first alternative small appliance 54i and/or the small appliance device 10i may be used for body care and/or for body treatment.

FIG. 16 shows a third alternative small appliance 54k in a perspective representation. The third alternative small appliance 54k comprises at least one small appliance device 10k. The third alternative small appliance 54k is embodied as an electric toothbrush. The small appliance device 10k is embodied as a toothbrush device, in particular as an electric toothbrush device.

The small appliance devices 10i-k of the exemplary embodiments of FIGS. 14-16 may in this case, of course, contain features of the small appliance devices 10a-h of the exemplary embodiments of FIGS. 1 to 13 in any desired combination.

The invention claimed is:

1. A small appliance device, having a drive unit which comprises at least one drive element, wherein the drive element comprises at least one magnetically shape-shiftable material and having a second drive unit, which is arranged antagonistically with respect to the drive unit.

2. The small appliance device as claimed in claim 1, wherein the magnetically shape-shiftable material is a magnetic shape-memory material.

3. The small appliance device as claimed in claim 1, wherein the magnetically shape-shiftable material is monocrystalline.

4. The small appliance device as claimed in claim 1, wherein the magnetically shape-shiftable material contains nickel, manganese and gallium.

5. The small appliance device as claimed in claim 1, wherein the drive element is implemented as a solid body.

6. The small appliance device as claimed in claim 1, wherein the drive unit comprises at least one magnet unit, which is configured to generate at least one time-variable shape-shiftable magnetic field for the drive element.

7. The small appliance device as claimed in claim 6, wherein the magnet unit comprises at least one coil element, which at least partially encompasses the drive element.

8. The small appliance device as claimed in claim 6, wherein the magnet unit is configured to initiate a contraction of the drive element parallel to an actuation direction.

9. The small appliance device as claimed in claim 1, comprising a reset unit, which is configured to apply a reset force onto the drive element.

10. The small appliance device as claimed in claim 9, wherein the reset unit is configured to counteract a contraction of the drive element parallel to an actuation direction.

11. The small appliance device as claimed in claim 9, wherein the reset unit comprises at least one reset element having a degressive spring characteristic curve.

12. The small appliance device as claimed in claim 9, wherein the reset unit comprises at least one magnet element.

13. The small appliance device as claimed in claim 1, comprising at least one holding unit, which is configured to stabilize the first stable expansion state and the second stable expansion state, and which comprises at least one holding magnet element.

14. The small appliance device as claimed in claim 13, wherein the holding magnet element comprises at least one magnetically reversible permanent magnet.

15. The small appliance device as claimed in claim 1, wherein the second drive unit comprises at least one second drive element, which comprises at least one magnetically shape-shiftable material.

16. The small appliance device as claimed in claim 1, comprising at least one reluctance unit, which is configured to generate an assisting drive force and/or an assisting drive movement.

17. The small appliance device as claimed in claim 16, wherein the drive unit comprises at least one support element for the drive element, which is at least partially embodied integrally with the reluctance unit.

18. The small appliance device as claimed in claim 1, wherein the drive unit comprises at least one further drive element, which is connected in series with the drive element in respect of a drive effect, and the longitudinal axis of which is different to a longitudinal axis of the drive element.

19. The small appliance device as claimed in claim 1, comprising at least one energy supply unit, which comprises at least one energy store, having at least one capacitor and/or at least one battery.

20. A small appliance having at least one small appliance device as claimed in claim 1.

21. A use of a small appliance device as claimed in claim 1 for body care and/or for body treatment.

22. A method with at least one small appliance device as claimed in claim 1, wherein at least one body-care activity and/or at least one body treatment is carried out.

23. The small appliance as claimed in claim 20, implemented as a body-care appliance.

24. The small appliance as claimed in claim 23, implemented as a shaver, a beard-trimmer, a hair-trimmer, an epilating appliance, a tattooing appliance or a toothbrush.

* * * * *